(12) United States Patent
Hamamoto et al.

(10) Patent No.: US 9,980,920 B2
(45) Date of Patent: *May 29, 2018

(54) BASE COMPOSITION FOR TAPE AGENT

(71) Applicant: MEDRX CO., LTD., Kagawa (JP)

(72) Inventors: Hidetoshi Hamamoto, Kagawa (JP); Katsuhiro Yamanaka, Kagawa (JP); Takahiro Tanimoto, Kagawa (JP)

(73) Assignee: MEDRx Co., Ltd., Kagawa (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/917,908

(22) PCT Filed: Sep. 10, 2014

(86) PCT No.: PCT/JP2014/073996
§ 371 (c)(1),
(2) Date: Mar. 9, 2016

(87) PCT Pub. No.: WO2015/037639
PCT Pub. Date: Mar. 19, 2015

(65) Prior Publication Data
US 2016/0220506 A1 Aug. 4, 2016

(30) Foreign Application Priority Data

Sep. 11, 2013 (JP) .................................. 2013-188886

(51) Int. Cl.
*A61K 9/70* (2006.01)
*A61K 45/00* (2006.01)
*A61K 31/165* (2006.01)
*A61K 31/485* (2006.01)
*A61K 38/00* (2006.01)

(52) U.S. Cl.
CPC .......... *A61K 9/7053* (2013.01); *A61K 31/165* (2013.01); *A61K 31/485* (2013.01); *A61K 45/00* (2013.01); *A61K 38/00* (2013.01)

(58) Field of Classification Search
CPC .... A61K 9/7053; A61K 45/00; A61K 31/485; A61K 38/00
See application file for complete search history.

(56) References Cited

U.S. PATENT DOCUMENTS

| 5,676,968 | A | 10/1997 | Lipp et al. |
| 5,866,157 | A | 2/1999 | Higo et al. |
| 6,326,421 | B1* | 12/2001 | Lipman .................... A61L 15/58 428/355 BL |
| 6,503,532 | B1 | 1/2003 | Murty et al. |
| 2004/0028724 | A1 | 2/2004 | Terahara et al. |
| 2004/0086552 | A1 | 5/2004 | Klokkers et al. |
| 2005/0215727 | A1* | 9/2005 | Feldstein ................ A61K 8/042 525/326.9 |
| 2008/0299228 | A1* | 12/2008 | Harris .................. A61K 9/0014 424/709 |
| 2009/0123526 | A1 | 5/2009 | Kuribayashi |
| 2010/0256174 | A1* | 10/2010 | Yamaguchi .......... A61K 9/0014 514/282 |
| 2011/0008398 | A1* | 1/2011 | Morimoto ............ A61K 9/7061 424/400 |
| 2011/0028880 | A1 | 2/2011 | Uchida et al. |
| 2015/0174249 | A1* | 6/2015 | Hamamoto ........ A61K 31/7088 514/11.9 |

FOREIGN PATENT DOCUMENTS

| EP | 1269999 | A1 | 1/2003 |
| EP | 2223703 | A1 | 9/2010 |
| JP | H06-145050 | A | 5/1994 |
| JP | H07-506083 | A | 7/1995 |
| JP | H07-215850 | A | 8/1995 |
| JP | 2003-128859 | A | 5/2003 |
| JP | 2007-269753 | A | 10/2007 |
| JP | 2009-519886 | A | 5/2009 |
| JP | 2011-074035 | A | 4/2011 |
| JP | 2012-158571 | A | 8/2012 |
| JP | 2012-158571 | * | 9/2012 ............... A61K 9/70 |

(Continued)

OTHER PUBLICATIONS

Neusilin—Oct. 2007.*
International Preliminary Report on Patentability and Written Opinion issued in corresponding International Patent Application No. PCT/JP2014/073996 dated Mar. 24, 2016.
Extended European Search Report issued in corresponding European Patent Application No. 14843847.6 dated Aug. 9, 2016.
International Search Report issued in corresponding International Patent Application No. PCT/JP2014/073996 dated Nov. 18, 2014.
Office Action issued in corresponding Japanese Patent Application No. 2015-536608 dated Apr. 17, 2018.

*Primary Examiner* — Sean M Basquill
(74) *Attorney, Agent, or Firm* — Morgan, Lewis & Bockius LLP

(57) ABSTRACT

The present invention provides a composition for a non-aqueous patch preparation having an excellent adhesibility which can sustainedly release a drug. The patch preparation of the present invention can improve the adhesibility thereof as well as the release property of a drug by the addition of powder ingredient (e.g. a filler). As a result, the long-time sustention of the adhesibility of patch preparations can achieve the improvement of the transdermal absorbability and the sustained release of a drug. By the use of a composition for a patch preparation comprising this powder ingredient, a drug, regardless of the type of a drug is dissolved in an organic solvent or an ionic liquid to prepare a drug solution comprising the organic solvent, the drug solution is incorporated into the non-aqueous patch preparation of the present invention, and thereby a preparation with the improved transdermal-absorbability and sustained release can prepared.

12 Claims, 7 Drawing Sheets

(56) References Cited

FOREIGN PATENT DOCUMENTS

| JP | 2012-176943 A | 9/2012 |
|---|---|---|
| JP | 2013-119528 A | 6/2013 |
| WO | 96/16642 A1 | 6/1996 |
| WO | 02/03969 A2 | 1/2002 |
| WO | 02/38139 A1 | 5/2002 |
| WO | 2007/071526 A1 | 6/2007 |
| WO | 2009/066457 A1 | 5/2009 |
| WO | 2009/107479 A1 | 9/2009 |
| WO | 2010/113225 A1 | 10/2010 |
| WO | 2013/191187 A1 | 12/2013 |

* cited by examiner (Release property of drug is composed of biphasic release behaviors.)

BASE COMPOSITION FOR TAPE AGENT

TECHNICAL FIELD

The present invention relates to a composition for a plaster base material comprising a filler. Particularly, the present invention relates to a composition for a plaster base material in a non-aqueous tape preparation prepared by solvent method.

BACKGROUND ART

In order to prepare a composition for a patch preparation comprising a drug, a set of processes of dissolving a drug in a solvent such as an organic solvent, diluting the drug solution with a volatile solvent such as toluene and hexane which is easily evaporated, mixing the solution with an adhesive, extending the mixture product, and evaporating the volatile solvent to prepare a composition for a patch preparation (solvent method) have been typically used. In such case, the organic solvent used therein has been employed for serving as a transdermal absorption promoter as well as for dissolving a drug.

However, when a large volume of an organic solvent is used for dissolving a drug, the organic solvent can soften an adhesive layer in a tape preparation. As a result, the adhesibility of the tape preparation can be decreased, and also a part of an adhesive used in the adhesive layer can remain on the skin when the tape preparation is removed from the skin. In order to prevent such trouble caused by using a large volume of organic solvent, fillers are added to an adhesive to improve the lowered adhesibility (e.g. Patent Document 1).

Recently, some attempts to use a fatty acid-based ionic liquid as a solution for dissolving a drug or a transdermal absorption promoter have been made (e.g. Patent Document 2). However, a plaster base material used in a tape preparation is a SIS-based lipophilic plaster base material which has less affinity for a fatty acid based-ionic liquid because a fatty acid based-ionic liquid is in a salt form with high polarity, and thus such plaster base material has a tendency to be less miscible with the ionic liquid. As a result, a drug solution in which a drug is dissolved mainly in a fatty acid based-ionic liquid has a tendency to be easily separated from a lipophilic plaster base material.

Although a variety of means for solving these problems have been studied until now, drastic means have not been found.

PRIOR ART DOCUMENTS

Patent Documents

Patent Document 1: JP 07-215850
Patent Document 2: JP 2009-066457

SUMMARY OF THE INVENTION

Problem to be Solved by the Invention

An object of the present invention is to provide a novel lipophilic plaster base material (adhesive layer) prepared by using a filler that is insoluble both in the adhesive layer and in an organic solvent, wherein the filler is dispersed, and spaces (voids) are formed between the plaster base material and the filler or spaces (voids) are formed between the fillers. Furthermore, an object of the present invention is to provide a plaster base material (adhesive layer) for a non-aqueous tape preparation which retains a drug solution comprising an active pharmaceutical ingredient in the spaces (voids) formed by the fillers, and thereby improves the adhesibility of the tape preparation and the release property of the drug.

Means for Solving the Problems

The present inventors have found that by the addition of a filler (powder) to a non-aqueous patch preparation (tape preparation) containing a conventional fatty acid-based ionic liquid, the sustained-release property of a drug solution can be produced along with the improvement of the adhesibility of an adhesive layer (PCT/JP2013/66765). Furthermore, the present inventors have studied the material quality of the filler (powder) to be added and the amount thereof as well as a combination of the fillers and the composition thereof, and thus the following findings can be produced.

a) The present inventors have found that, in order to form spaces (voids) between fillers (powder) for retaining a solvent in a plaster base material (adhesive layer), it is necessary to add an approximate amount of the powder on the basis of the weight of the plaster base material (adhesive layer) as shown in the following inequality, which can be an index of the bulk density of the powder.

$$0.2 \times (\text{the weight of the adhesive layer}) \times (\text{the bulk density of the powder}) \leq \text{the amount of the powder to be added} \leq 0.6 \times (\text{the weight of the adhesive layer}) \times (\text{the tap density of the powder})$$

b) One or more types of powders can be used for forming the spaces (voids) between the fillers (powder). When two or more types of the powders are combined, it is preferable to use a mixture of powder having a large particle size and powder having a small particle size. The present inventors have found that the preferred amount of the powder having a large particle size (a small bulk density) is 20 to 30%.

c) The spaces (voids) between the fillers (powder) denote the volume which can retain a solvent therein. When the practical volume of the solvent exceeds the approximate amount (volume) thereof as shown in the following inequality, the solvent exudes onto the surface of an adhesive layer in a tape preparation, and then the adhesibility of the tape preparation can be decreased.

$$\frac{\text{the amount of the solvent to be added}}{(\text{the volume of the solvent to be added})} < \frac{\dfrac{\text{the amount of the powder to be added}}{\text{the tap density of the powder}}}{(\text{the volume of the powder to be added})} \times 1.2$$

d) By making the composition suited as mentioned above, various non-aqueous tape preparations containing powder can be prepared, which can control two specific properties of the immediate-release and sustained-release properties of a drug as shown in FIG. 13, and thus preparations having the desired release property can be prepared.

The present inventors have found that even when an ionic liquid or a mixture of an ionic liquid and an organic solvent is used in a tape preparation, a drug solution can be retained in spaces between powder or in spaces between powder and plaster base by adding a lipophilic plaster base and a powder which is insoluble both in an ionic liquid and in an organic solvent to a conventional tape preparation, and thereby, to prevent the drug solution from being released from the plaster base. As a result, the present inventors have found that the drug solution does not uselessly exude onto the surface of the tape preparation, and thus the adhesibility of the tape preparation and the release property of the drug can be improved. In addition, the present inventors have found that even when an ionic liquid is encompassed into a lipophilic plaster base material (adhesive layer) as droplets, the drug solution can be released onto the surface of the plaster base via the spaces between the powder or the spaces between the powder and the plaster base which are formed by the addition of the powder, and thus the release property of the drug can be improved.

The present inventors have completed the present invention on the basis of the above findings.

The subject matters of the present invention are as follows.

(1) A composition for a non-aqueous patch preparation comprising a drug, an organic solvent, and a powder which is insoluble both in the organic solvent and in a lipophilic plaster base material, wherein the powder for an adhesive layer is contained as shown in the following inequality:

0.2×(the weight of the adhesive layer)×(the bulk density of the powder)≤the amount of the powder to be added≤0.6×(the weight of the adhesive layer)×(the tap density of the powder).

(2) The composition according to the above item (1), wherein the powder is at least one selected from the group consisting of crystalline cellulose, anhydrous silicic acid, starch, carmellose, carmellose metal salt, kaolin, agar, carrageenan, pectin, and powdered sugar.
(3) The composition according to the above item (1) or (2), wherein the powder is a mixture of powders.
(4) The composition according to the above item (3), wherein the mixture comprises 20 to 30 w/w % of anhydrous silicic acid.
(5) The composition according to any one of the above items (1) to (4), wherein the organic solvent comprises a fatty acid-based ionic liquid and/or a salicylic acid-based ionic liquid.
(6) The composition according to the above item (5), wherein the fatty acid-based ionic liquid is an equimolar salt of a saturated or unsaturated fatty acid having 3 to 22 carbon atoms and an alkanolamine having 6 to 9 carbon atoms.
(7) The composition according to the above item (5) or (6) further comprising a saturated or unsaturated fatty acid having 10 to 22 carbon atoms.
(8) The composition according to the above item (7), wherein the saturated or unsaturated fatty acid having 3 to 22 carbon atoms is at least one selected from the group consisting of lactic acid, levulinic acid, decanoic acid, oleic acid, isostearic acid, and myristic acid.
(9) The composition according to the above item (5), wherein the alkanolamine is at least one selected from the group consisting of triethanolamine, triisopropanolamine, and diisopropanolamine.
(10) The composition according to the above item (5), wherein the fatty acid-based ionic liquid and/or the salicylic acid-based ionic liquid are at least one selected from the group consisting of triethanolamine lactate, triisopropanolamine lactate, triethanolamine levulinate, diisopropanolamine levulinate, triisopropanolamine decanoate, triethanolamine salicylate, diisopropanolamine oleate, triethanolamine isostearate, diisopropanolamine isostearate, and diisopropanolamine myristate.
(11) The composition according to any one of the above items (1) to (10), wherein the lipophilic plaster base material comprises an elastomeric styrene-isoprene-styrene block copolymer.
(12) The composition according to any one of the above items (1) to (11), wherein the drug is selected from a small molecular medicinal compound, a protein medicine, an antigen peptide, or a nucleic acid derivative.
(13) The composition according to any one of the above items (1) to (12), wherein the organic solvent is contained as shown in the following inequality:

$$\frac{\text{the amount of the solvent to be added}}{\text{(the volume of the solvent to be added)}} < \frac{\frac{\text{the amount of the powder to be added}}{\text{the tap density of the powder}}}{\text{(the volume of the powder to be added)}} \times 1.2$$

(14) The composition according to any one of the above items (1) to (13) further comprising a diester and/or a triester.
(15) The composition according to any one of the above items (1) to (14) wherein the diester is at least one selected from the group consisting of diethyl sebacate, diisopropyl adipate, and diisobutyl adipate, and the triester is at least one selected from the group consisting of medium-chain triglyceride and triacetin.

Effects of the Invention

The composition for a non-aqueous patch preparation of the present invention relates to a non-aqueous patch preparation (tape preparation) comprising a drug solution in which a drug is dissolved in an organic solvent (mainly comprising an fatty acid-based ionic liquid), a lipophilic plaster base material, and a powder. By the addition of powder, the drug solution with high polarity can be retained in the spaces between the powder formed in the lipophilic plaster base material to avoid releasing the drug solution from the lipophilic plaster base material and exuding onto the surface of the plaster base. As a result, the deterioration in the adhesibility of the tape preparation can be prevented. In addition, the release property and utilization rate of a drug can be improved because the routes for releasing the drug solution out of the plaster base are secured with said spaces.

As described above, the decrease in the adhesibility of a tape preparation caused by the use of an organic solvent with high polarity for dissolving a drug (mainly comprising an fatty acid-based ionic liquid), which has been a problem in conventional tape preparations, can be improved by using powder in a tape preparation, and also the release property and utilization rate of a drug can be greatly improved. Thus, such long-time sustention of the adhesibility of tape preparations can achieve the improvement of the transdermal absorbability and the sustained release of a drug.

Also, the adhesibility of the lipophilic plaster base material to a backing support body (a backing) can be enhanced by the addition of a diester and/or a triester to the organic solvent, and thus the backing support body is not removed from the plaster base material in the tape preparation.

BRIEF DESCRIPTION OF THE DRAWINGS

FIG. 1 shows that the powder is dispersed into the lipophilic plaster base material (oil-soluble plaster base), and the drug solution is retained in the spaces between the powder or in the spaces between the powder and the plaster base. Furthermore, FIG. 1 shows that quite-narrow channels for releasing the drug solution from the inside of the plaster base onto the surface thereof are formed by connecting these spaces to each other. The parts in which the powder is present on the surface of the plaster base cause the exudation of the drug solution from the spaces around the powder, whereas the parts in which the powder is not present on the surface of the plaster base cause less exudation or less release of the drug solution. As a result, the deterioration of the adhesibility of the patch preparation is prevented as a whole. FIG. 1 also shows the above.

FIG. 2 is a diagram showing the correlation between the emission amount of the blue pigment and the volume ratio of the powder to the plaster base material (the volume of the powder/the volume of the lipophilic plaster base material). The volume of the powder was calculated based on the bulk density thereof.

FIG. 7 shows that the amount of light silicic acid is preferably 1 to 5 w/w %, and more preferably 2.5 to 5 w/w %.

FIG. 8 shows that the amount of crystalline cellulose is preferably 2.5 to 18 w/w %, and more preferably 5 to 15 w/w %.

FIG. 9 shows that the amount of corn starch is preferably 20 to 42 w/w %, and more preferably 29 to 42 w/w %.

FIG. 10 is described in Kimio KAWAKITA et al., *Bulletin of the Faculty of Engineering*, Hosei University 2, pages 47-53.

FIG. 11 shows that the tape preparation containing the powders has the sustained-release property of the drug.

FIG. 12 shows that the drug blood level reaches a peak two hours after the preparation was applied to the skin, and then is rapidly decreased. FIG. 12 shows the change in the drug blood level which is greatly different from that of FIG. 11.

DETAILED DESCRIPTION OF THE PREFERRED EMBODIMENTS

Figure 1:
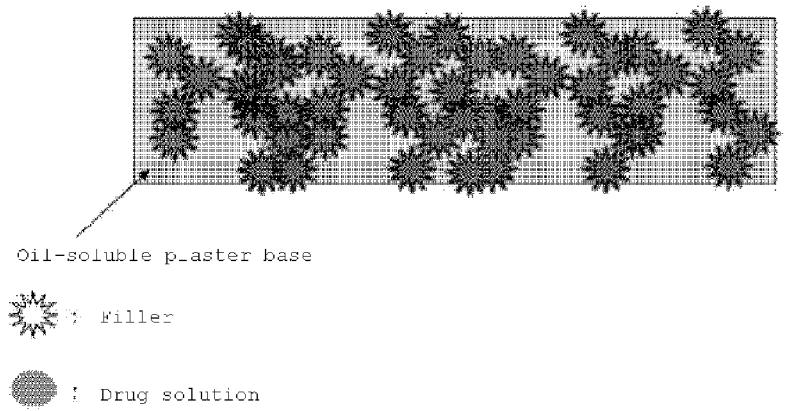
FIG. 1 is a conceptual diagram showing a cross-section of the plaster base in the non-aqueous patch preparation (tape preparation) of the present invention.

The term "drug" in the present invention denotes a drug for medical use selected from a small molecular medicinal compound, a protein medicine, an antigen peptide, or a nucleic acid derivative. Many of the drugs used herein have hydrophilic residue(s) as a main substituent (or drugs in a salt form thereof). Thus, such drugs are less soluble in a lipophilic plaster base material. For such unfavorable insolubility, an ionic liquid with high polarity is used to dissolve the drug, and the solution of the drug in the ionic liquid is used as a drug solution. Among the drugs of the present invention, for example, a small molecular medicinal compound denotes a drug having an acidity ("acidic drug") or a drug having a basicity ("basic drug").

The term "acidic drug" herein denotes a drug which has a carboxylic acid as a functional group and has an acidity as a whole of the compound. Examples of the acidic drug include non-steroid anti-inflammatory drugs (NSAIDs) such as indomethacin, ketoprofen, ibuprofen, flurbiprofen, diclofenac, etodolac, and loxoprofen; anti-allergic drugs such as tranilast, cromoglicic acid, and pemirolast; sedative hypnotic drugs or anti-anxiety drugs such as amobarbital, secobarbital, and phenobarbital; and muscle relaxant drugs such as dantrolene, and mivacurium. Preferred examples of the acidic drug include indomethacin, flurbiprofen, ketoprofen, etodolac, ibuprofen, loxoprofen, and diclofenac.

The term "basic drug" herein denotes a drug which has a primary, secondary, or tertiary amine structure as a functional group and has a basicity as a whole of the compound. Examples of the basic drug include topical anesthetic drugs such as lidocaine, dibucaine, bupivacaine, procaine, mepivacaine, bupivacaine, and tetracaine; anti-histamine drugs such as diphenhydramine; analgesic drugs such as tramadol; anti-spasmodic drugs such as eperisone; muscle relaxant drugs such as tolperisone; antitussive drugs such as dextromethorphan; acetylcholine decomposition inhibitors such as donepezil; and opioid analgesic drugs such as morphine, codeine, naloxone, fentanyl, and oxycodone. Preferred examples of the basic drug include lidocaine, tolperisone, bupivacaine, eperisone, tramadol, morphine, and donepezil.

The term "protein medicine" herein denotes a protein for medical use. Examples of the protein medicine include various recombinant proteins and modified proteins which are relatively small molecules. Examples of various recombinant proteins and modified proteins include insulin, human growth hormone, elcatonin, calcitonin, EGF, VEGF, and GLP-1.

The term "antigen peptide" herein denotes an antigenic fragment derived from a foreign microbe or a tumor cell which is used for stimulating immunity. Examples of the antigen peptide include WT-1, and human papillomavirus.

The term "nucleic derivative" herein denotes a general term for DNA and RNA which are used as a medicinal ingredient. The DNA used herein is not especially limited as long as it is DNA for gene therapy. Examples of the nucleic derivative include DNA vaccine, antisense, ribozyme, aptamer, and siRNA.

The term "fatty acid-based ionic liquid" in the present invention denotes a Brønsted salt prepared from a fatty acid having 3 to 22 carbon atoms and a alkanolamine compound having 6 to 9 carbon atoms, which is in a viscous liquid form at ambient temperature.

The term "salicylic acid-based ionic liquid" in the present invention denotes a Brønsted salt prepared from salicylic acid and an alkanolamine compound having 6 to 9 carbon atoms, which is in a viscous liquid form at ambient temperature.

Preferably, in order to enhance the skin permeability of a drug, the ionic liquid used in a drug solution is in the state that the drug solubility of the drug solution is close to saturation. Thus, the drug solubility of the drug solution can be controlled through the addition of one or more saturated or unsaturated fatty acids having 3 to 22 carbon atoms or a combination of various fatty acid-based ionic liquids.

The "fatty acid-based ionic liquid and/or salicylic acid-based ionic liquid" in the present invention include an equilibrium mixture of each equimolar amount of an organic carboxylic acid and an amine compound, besides a Brønsted salt. Preferred examples of the ionic liquid include triethanolamine lactate, triisopropanolamine lactate, triethanolamine salicylate, triisopropanolamine salicylate, triisopropanolamine decanoate, triethanolamine decanoate, diisopropanolamine decanoate, diisopropanolamine oleate, triethanolamine isostearate, diisopropanolamine isostearate, and a mixture thereof.

The term "drug solution" in the present invention denotes a solution in which a drug is dissolved in an organic solvent. Also, the drug solution denotes a solution further comprising an ionic liquid as a solubilizing agent for the drug or a transdermal absorption accelerator. The drug solution of the present invention typically comprises an ionic liquid with high drug solubility. Also, the organic solvent used herein is required to be miscible with the ionic liquid. Thus, a polar organic solvent can be typically used. For example, alcohols such as propylene glycol and/or esters such as diethyl sebacate and isopropyl myristate can be used.

The term "powder" in the present invention denotes a solid powdered reagent which is insoluble and immiscible both in a drug solution and in a lipophilic plaster base material (oil-soluble plaster base material). Specifically, the powder is a solid powdered reagent which is insoluble in a solvent such as an organic solvent in the drug solution even though the powder swells due to the absorption of the solvent. Examples of the powder include a solid powdered reagent (filler) used in a plaster base in a patch preparation such as anhydrous silicic acid, crystalline cellulose, zinc oxide, titanium oxide, kaolin, and calcium carbonate. Furthermore, examples of the powder include flour, starch powder such as corn starch, carmellose, carmellose metal salt, agar, carrageenan, pectin, powdered sugar, polyethylene powder, and polystyrene sulfonate. Preferred examples of the powder include crystalline cellulose, anhydrous silicic acid, starch, carmellose, and carmellose metal salt. The adhesibility of the patch preparation can be improved with increasing the amount of the powder of the present invention. Whereas, when the powder is excessive in amount, the patch preparation becomes hard, and the adhesibility of the patch preparation is deteriorated. Thus, in order to form spaces (voids) between the powder for retaining a solvent in a plaster base material (adhesive layer), it is necessary to add the preferred amount of the powder on the basis of the weight of the plaster base material (adhesive layer) as shown in the following inequality, which can be an index of the bulk density of the powder.

$$0.2 \times (\text{the weight of the adhesive layer}) \times (\text{the bulk density of the powder}) \leq \text{the amount of the powder to be added} \leq 0.6 \times (\text{the weight of the adhesive layer}) \times (\text{the tap density of the powder}).$$

In addition, one or more types of powders can be used for forming the spaces (voids) between the powders. When two or more types of the powders are combined, it is preferable to use a mixture of powder having a large particle size and powder having a small particle size. In such case, it is preferable that the amount of the powder having a large particle size (i.e., having a small bulk density) is 20 to 30%.

Also, the spaces (voids) between the powder denote the volume which can retain a solvent (drug solution) in a plaster base material (adhesive layer). The volume is shown in the following inequality. When the practical amount of an organic solvent to be added exceeds the volume as shown below, the solvent (drug solution) exudes onto the surface of the adhesive layer, and then the adhesibility of the preparation can be decreased.

$$\frac{\text{the amount of the solvent to be added}}{(\text{the volume of the solvent to be added})} < \frac{\frac{\text{the amount of the powder to be added}}{\text{the tap density of the powder}} \times 1.2}{(\text{the volume of the powder to be added})}$$

Figure 13:
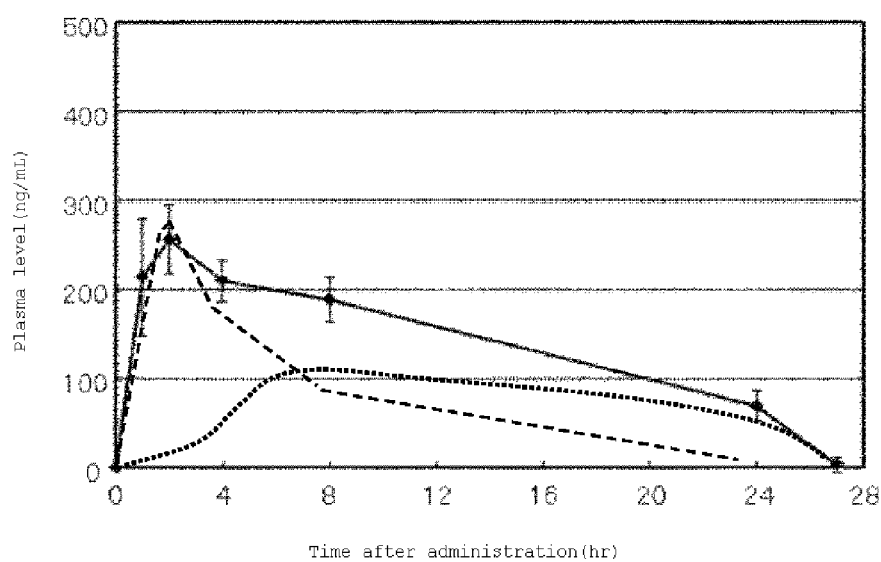
FIG. 13 is a diagram showing that the change in drug the blood level over time as shown in FIG. 11, which is composed of biphasic properties of the immediate-release and sustained-release properties of the drug.

Thus, the immediate-release and sustained-release properties of a drug in a non-aqueous tape preparation containing powder can vary depending on the changes in the amount and composition of the powder. For example, preparations having a desired release property can be prepared by controlling two specific properties of the immediate-release and sustained-release properties of a drug as shown in FIG. 13.

In order to control the immediate-release and sustained-release properties of a drug, the spaces to be formed can be properly controlled by combining various powders having different bulk densities. For example, a combination of 20 to 30 w/w % of anhydrous silicic acid having a small bulk density, and crystalline cellulose or corn starch having a large bulk density may be used as a mixture of powders.

The term "powder which is insoluble both in the drug solution and in the lipophilic plaster base material" in the present invention means that a powder is insoluble both in an organic solvent and an ionic liquid, and insoluble in a lipophilic plaster base so that the spaces between the powder formed in the lipophilic plaster base can be retained. The term "insoluble" is used in the sense of insolubility, and means that 1 mg of powder cannot be dissolved in 10 g of an organic solvent or a lipophilic plaster base, according to the definition of solubility in the U.S. (the U.S. Pharmacopeia National Formulary).

The term "organic solvent" in the present invention denotes a solvent that is miscible with an ionic liquid, which is used for preparing a drug solution in which a drug is dissolved in combination with the ionic liquid. The organic solvent in the present invention can be also used as a transdermal absorption accelerator. Furthermore, the organic solvent can be also used for dispersing the organic carboxylic acid-based ionic liquid in which a drug is dissolved into the plaster base. Examples of the organic solvent in the present invention include alcohols such as ethanol, propanol, and oleyl alcohol; polyalcohols such as ethylene glycol, propylene glycol, 1,3-butanediol, polyethylene glycol (macrogol), and glycerin; and esters such as diethyl sebacate, isopropyl myristate, propylene carbonate, and diisopropyl adipate. In addition, the organic solvent includes fatty acids such as lactic acid, levulinic acid, decanoic acid, oleic acid, myristic acid, and isostearic acid. These organic solvents may be used in suitable combination to achieve the above purposes. More preferably, polyalcohols such as propylene glycol, 1,3-butanediol, polyethylene glycol, and glycerin can be used in combination with esters such as diethyl sebacate, isopropyl myristate, propylene carbonate, and medium-chain triglyceride.

Among the above organic solvents, the solvent retained in the spaces (voids) formed by powder is mainly a solvent which is hard to dissolve an adhesive layer (lipophilic plaster base material) (e.g. a solvent which is less compatible with the adhesive layer). Examples of the solvent which is less compatible with the adhesive layer include an alcohol solvent (e.g. macrogol, propylene glycol, and polyethylene glycol) and a protic solvent such as a fatty acid-based ionic liquid and a fatty acid. On the other hand, an ester solvent (e.g. diethyl sebacate and isopropyl myristate) is more compatible with the adhesive layer (lipophilic plaster base material), and thus it has a tendency to be hard to be retained in the spaces (voids) in the adhesive layer. Thus, in studying the volume of the solvent retained in the spaces (voids) formed by the powder to keep the adhesibility of a preparation, the volume of the solvent which is less compatible with the adhesive layer should be mainly evaluated.

The term "lipophilic plaster base material" in the present invention denotes a plaster base (adhesive) comprising a lipophilic polymer as a main component. The plaster base is composed of an elastomer and a lipophilic (hydrophobic) adhesive, in which a drug solution is dispersed or emulsified into the plaster base. When the plaster base is composed of an elastomer and a lipophilic (hydrophobic) adhesive, it can be used as a non-aqueous tape preparation (plaster). When the plaster base is composed of an elastomer and a hydrophilic adhesive, it can be used as an aqueous patch preparation (cataplasm). As described above, the lipophilic plaster base material is composed of various reagents such as an elastomer, a tackifier, and a softening filler.

Examples of the elastomer include synthetic rubbers such as a styrene-isoprene-styrene copolymer (SIS), a silicon rubber, polyisobutylene, a polystyrene-butadiene copolymer, and polyisobutylene; acrylic acid resins such as alkyl acrylate and alkyl methacrylate; and natural rubbers.

The tackifier denotes a reagent which can be added into the elastomer such as a SIS resin to enhance the adhesibility of a patch preparation to the skin. Examples of the tackifier include a polyterpene resin, a polyolefin resin (e.g. Plastibase®), a polystyrene resin, an aromatic petroleum resin, rosin, and hydrogenated rosin. Preferred examples of the tackifier include a polyterpene resin and a polyolefin resin (e.g. Plastibase®).

The softening agent is a reagent which can be added to make the elastomer such as a SIS resin and the adhesive flexible. Examples of the softening agent include petroleum-based softening agents such as polybutene, polyisobutylene, and process oil; fatty oil-based softening agents such as palm oil and castor oil; purified lanolin; and liquid paraffin. Preferred examples of the softening agent include polybutene and liquid paraffin.

The patch preparation of the present invention may further comprise additives such as an antioxidant, a surfactant, a thickening agent, and a surfactant as long as the effects of the present invention are not prevented. As the suitable additives, commercially available reagents may be used for any purpose.

Examples of the antioxidant include organic antioxidants such as BHT, propyl gallate, and sodium ascorbate; and inorganic antioxidants such as sodium thiosulfate, sodium bisulfite, sodium sulfite, and sodium pyrosulfite.

In addition, a thickening agent such as Carbopol®, an ultraviolet absorbing agent, and/or powders may be added.

Examples of the surfactant can include a non-ionic surfactant, an anionic surfactant, a cationic surfactant, and an amphoteric surfactant. Examples of the non-ionic surfactant include sorbitan monolaurate, sorbitan monopalmitate, sorbitan sesquioleate, glycerin monostearate, decaglyceryl monolaurate, hexaglycerin polyricinoleate, polyoxyethylene (9) lauryl ether, polyoxyethylene (2) lauryl ether, polyoxyethylene (4,2) lauryl ether, polyoxyethylene (5) nonylphenyl ether, polyoxyethylene (7,5) nonylphenyl ether, polyoxyethylene (10) nonylphenyl ether, polyoxyethylene (3) octylphenyl ether, polyoxyethylene (10) octylphenyl ether, polyoxyethylene (10) oylelamine, polyoxy (5) oleylamine, polyoxy (5) oleic amide, polyoxyethylene (2) monolaurate, monoglyceride stearate, and polyoxyethylene castor oil (hydrogenated castor oil).

Examples of the anionic surfactant include sodium lauryl sulfate, potassium lauryl sulfate, triethanolamine lauryl sulfate, sodium cetyl sulfate, sodium lauroyl sarcosinate, sodium di-2-ethylhexyl sulfosuccinate, sodium polyoxyethylene (10) lauryl ether phosphate, sodium polyoxyethylene (4) lauryl ether phosphate, sodium polyoxyethylene (5) cetyl ether phosphate, and sodium polyoxyethylene (6) oleyl ether phosphate.

Examples of the cationic surfactant include stearyl trimethylammonium chloride, distearyl dimethylammonium chloride, benzalkonium chloride, and stearyl dimethyl benzylammonium chloride.

Examples of the amphoteric surfactant include betaine lauryldimethylaminoacetate and 2-alkyl-N-carboxymethyl-N-hydroxyethyl imidazolinium betaine. Lauroyl diethanolamide may also be used as the amphoteric surfactant.

In addition, a thickening agent such as Carbopol®, an ultraviolet absorbing agent, and/or powders may be added.

The term "patch preparation" in the present invention denotes a non-aqueous patch preparation (tape preparation) which does not contain water as an essential ingredient. As the plaster base in the patch preparation of the present invention, conventional bases, for example, an acrylic acid resin base, or a base of a SIS resin which contains reagents such as a tackifier and a softening agent can be used. Preferred examples of the base include a base in which a SIS resin is used as an elastomer.

As a method for preparing the patch preparation of the present invention, similar methods to those of adhesive tapes may be used. Examples of the method include a solvent-coating method. The solvent-coating method is a method which comprises preparing a plaster base composition comprising a drug (drug solution), and directly coating a backing support body with the composition followed by drying. Also, a method can be used which comprises once coating a release paper with the plaster base composition followed by drying, and then removing the paper followed by contact-pressing the composition on the paper to the backing.

The release paper can be used for protecting the adhesive layer. As examples of the paper, a polyethylene-coated quality paper, a polyolefin-coated glassine paper, a polyethylene terephthalate (hereinafter referred to as PET) film, a polypropylene film or the like, one side of which is treated with silicon, may be used.

In addition, an additive having a multiple ester such as a diester and a triester can be added into the patch preparation of the present invention. The adhesibility of an additive to a backing is decreased by mixing a powder with the additive. The present inventors have studied the problem and found that the additive having a multiple ester such as a diester and a triester can enhance the adhesibility of an additive to a backing support body (backing) in a tape preparation, and thus the removal of the backing in use can be prevented. Examples of the diester include diethyl sebacate, diisopropyl adipate, and diisobutyl adipate. Examples of the triester include medium-chain triglyceride and triacetin.

EXAMPLES

Hereinafter, the present invention will be described more specifically with reference to Examples. However, the present invention is not intended to be limited to them by any means.

Example 1

Measurement of the Bulk Density and the Tap Density of Filler (Powder)

(1) Measurement of the Bulk Density of Filler (Powder)

The bulk density of a powder (g/cm$^3$) is a ratio of the mass of the powder sample in an untapped (loose) state and the volume of the powder including the interparticle void volume. Thus, the bulk density of a powder depends on the particle density of the powder and the spatial array of particles within the powder layer.

a) Method:

The volume of a powder sample with the known mass added into a graduated cylinder through a sieve was measured to calculate the bulk density of the powder. Specifically, a powder was passed through a sieve with 1.0 mm or more meshes to crush an aggregate which may be formed during storage. About 100 g of a sample (m) was weighed with 0.1% accuracy, and the sample was carefully added into a dry 250 mL graduated cylinder (minimum scale value: 2 mL) without compaction. The upper surface of the powder layer is carefully floated without compaction to read the aerated bulk volume (V) of the powder to minimum scale value. The bulk density of the powder (g/mL) was calculated according to the formula m/V.

b) Measurement Result:

The measured results of JP corn starch, light anhydrous silicic acid (AEROSIL® 200), and crystalline cellulose (CEOLUS®) are shown in Table 1 below.

(2) Measurement of the Tap Density of Filler (Powder)

The tap density of a powder means the increased bulk density of the powder after a container containing the powder sample is mechanically tapped. The tap density of a powder is given by mechanically tapping a graduated cylinder or container for measurement containing the powder sample.

a) Method:

The initial volume or mass of powder is measured, and then a graduated cylinder or container for measurement containing the powder is mechanically tapped until the volume or mass shows little change to read the volume or mass of the tapped powder. The mechanical tapping is performed by lifting up the graduated cylinder or container, and then dropping it down a given distance under its own weight. Specifically, a 250 mL graduated cylinder (minimum scale value: 2 mL) with a mass of 220±44 g and a device for dropping down the graduated cylinder from a height of 3±2 mm at a tapped rate of 250±15 times/min are used.

In the same manner as the above (1), the bulk volume (V) of the powder is measured. The powder sample to be measured is tapped 10 times, 500 times, and 1250 times to read the corresponding bulk volumes V10, V500, and V1250 to the minimum scale value. When the difference between V500 and V1250 is less than 2 mL, V1250 is used as the tap volume. When the difference between V500 and V1250 exceeds 2 mL, tapping is repeated in increments of 1250 times for each time until the difference between succeeding measurements reaches less than 2 mL. The tap density of a powder (g/cm$^3$) is calculated according to the formula m/Vf in which Vf is the final tap volume of the powder.

b) Measurement Result:

The measured results of JP corn starch, light anhydrous silicic acid (AEROSIL® 200), and crystalline cellulose (CEOLUS®) are shown in Table 1 below.

TABLE 1

|  | Bulk Density | Tap Density |
| --- | --- | --- |
| AEROSIL ® 200 (light anhydrous silicic acid) | 0.04 | 0.09 |
| CEOLUS ® (crystalline cellulose) | 0.14 | 0.31 |
| JP corn starch | 0.50 | 0.73 |

The above bulk density and tap density of each powder mean the volume of AEROSIL®, CEOLUS®, or corn starch. For example, when 1 g of AEROSIL® 200 is used as the powder (filler), the powder occupies a volume of 25 cm$^3$ (calculated as the bulk density of the powder). Also, corn starch occupies a volume of 2 cm$^3$ (calculated as the bulk density of the powder).

If each specific gravity of AEROSIL®, CEOLUS®, and corn starch is in the same range, each volume of the powders denote the size of spaces (voids) formed by each powder. For example, it is shown that the spaces (voids) formed by AEROSIL® or CEOLUS® are large in size, whereas the spaces (voids) formed by corn starch is small in size.

When an excessive amount of light anhydrous silicic acid or crystalline cellulose is added to the adhesive layer of a preparation, the adhesive layer enters spaces (voids) between the powder, and thus the spaces (voids) show little change. On the other hand, when an excessive amount of powder forms spaces (voids) in the adhesive layer of a tape preparation, the tape preparation becomes hard, and the adhesibility of the tape preparation is deteriorated. Thus, when powder is added, it is required to optimize the weight ratio of the powder and the adhesive layer of the preparation. On the other hand, when powder is small in amount, little space (void) is formed, and thus the powder cannot sufficiently exert an effect thereof.

Example 2

Optimization of the Ratio of the Volume of Filler (Powder) and the Amount of Adhesive Layer (Tape Preparation Base Material)

The problem for effectively utilizing the spaces (voids) formed in the tape preparation base material is to determine the amount of a filler (powder) to be added into the adhesive layer of the preparation.

The amounts of the ingredients in the adhesive layer were maintained at an almost constant rate, and the amount of the powder to be added was increased. The amount of the powder to be added for forming spaces (voids) between the powder and releasing the drug solution via the spaces (voids) was investigated. The volume of the powder was calculated based on the amount of the powder to be added using the bulk density of the powder as shown in Example 1, and the association between the volumes of the powder and the adhesive layer was evaluated.

As shown in FIG. 1, the spaces (voids) between the powder are formed with increasing the amount of the powder to be added. As a result, a drug retained in the spaces (voids) is released from the surface of the adhesive layer (lipophilic adhesive plaster base) to the outside thereof via the spaces (voids). In order to confirm the release property of a drug (i.e., the spaces (voids) formed by the powder), by using brilliant blue FCF as an alternative to the drug, the release property of the pigment from the surface of the adhesive layer (lipophilic adhesive plaster base) was evaluated.

(1) Preparation of Adhesive Layer (Lipophilic Adhesive Plaster Base)

Each reagent was weighed according to the composition (part by weight) in Table 2 below, and brilliant blue FCF was dissolved in the solution of triethanolamine levulinate in macrogol 400 (weight ratio of 6:14) to prepare the drug solution. Following the conventional solvent method, terpene resin, styrene-isoprene-styrene copolymer (SIS), butylhydroxytoluene, and liquid paraffin were dissolved in toluene, and then the macrogol 400 solution (weight ratio 6:14) and light anhydrous silicic acid (AEROSIL® 200) were added thereto and mixed. Next, each mixture was applied on the silicone-coated PET film and dried. After removal of the toluene, the backing was laminated to prepare the tape preparations.

(2) Detection of the Release Property of Drug Solution (i.e., Spaces (Voids) Formed by Powder)

The prepared tape preparations were tested on the release property of brilliant blue FCF from the adhesive layer. Specifically, the prepared tape preparations were cut into 3×3 cm, dipped into a beaker containing 8 mL of purified water, and then incubated at 32° C. for 6 hours. Next, the emission of the blue pigment from each tape preparation of the example was measured by the absorption spectrum measurement method at a wavelength of 630 nm. The results are also shown in Table 2 below.

TABLE 2

|  | A1 | A2 | A3 | A4 | A5 | A6 | A7 | A8 |
|---|---|---|---|---|---|---|---|---|
| Drug Solution: | | | | | | | | |
| Brilliant blue FCF | 0.016 | 0.016 | 0.016 | 0.016 | 0.016 | 0.016 | 0.016 | 0.016 |
| Triethanolamine Levulinate/Macrogol 400 | 10 | 9.96 | 9.92 | 9.81 | 9.73 | 9.62 | 9.53 | 9.42 |
| Adhesive: | | | | | | | | |
| Triethanolamine Levulinate/Macrogol 400 | 10 | 9.96 | 9.92 | 9.81 | 9.73 | 9.62 | 9.53 | 9.42 |
| Terpene Resin | 38 | 37.85 | 37.70 | 37.26 | 36.97 | 36.54 | 36.22 | 35.78 |
| SIS | 20 | 19.92 | 19.84 | 19.61 | 19.46 | 19.23 | 19.06 | 18.83 |
| Liquid Parffin | 17 | 16.93 | 16.87 | 16.67 | 16.54 | 16.35 | 16.20 | 16.01 |
| Butylhydroxytoluene | 1 | 1.00 | 0.99 | 0.98 | 0.97 | 0.96 | 0.95 | 0.94 |
| (Total weight of adhesive layer) | 96.0 | 95.6 | 95.3 | 94.1 | 93.4 | 92.3 | 91.5 | 90.4 |
| Filler (Powder): | | | | | | | | |
| AEROSIL ® (Volume) | 0 | 0.37 (9.3) | 0.75 (18.6) | 1.86 (46.5) | 2.6 (65) | 3.7 (92.5) | 4.5 (112.5) | 5.6 (140) |
| Volume ratio of powder to adhesive layer (%) | 0 | 9.7 | 19.5 | 49.4 | 69.6 | 100.2 | 123.0 | 154.9 |
| Preparation Form: | good | good | good | good | good | good | bad | bad |
| Emission Amount (Absorbance/Measurement Wavelength 630 nm) | 0.008 | 0.019 | 0.061 | 0.211 | 0.211 | 0.190 | 0.143 | 0.219 |

[NOTE]
The volume of AEROSIL ® 200 was calculated according to the weight thereof/the bulk density thereof.

The "volume ratio of the powder to the adhesive layer" was calculated according to the specific gravity of the adhesive layer containing the drug solution defined as 1.

Figure 2:
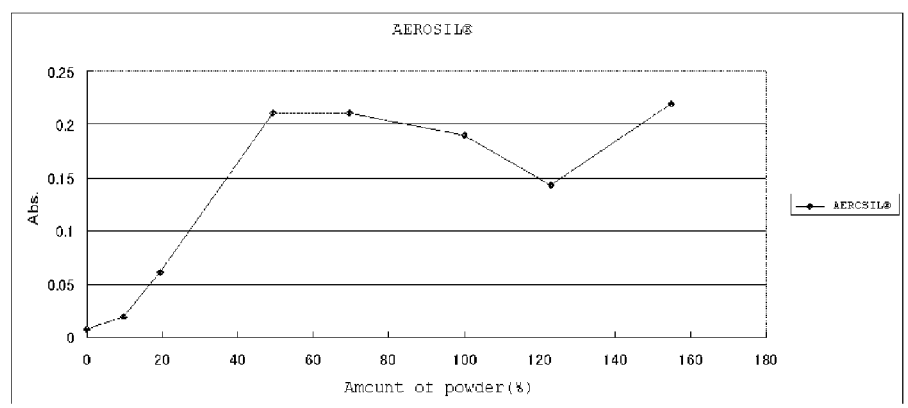
In FIG. 2, the blue pigment (brilliant blue FCF) was dissolved in the solution of triethanolamine levulinate in macrogol 400 (weight ratio of 6:14), light silicic acid as the powder was added thereto, the solution was mixed with the lipophilic plaster base material, and then the mixture product was extended to prepare the tape preparation following the conventional solvent method. The tape preparation was cut into 3×3 cm, dipped into a beaker containing 8 mL of purified water, and then incubated at 32° C. for 6 hours. The emission amount of the blue pigment from the sample was measured by the absorption spectrum measurement method at a wavelength of 630 nm.

FIG. 2 is a diagram showing the emission amount of brilliant blue FCF as shown in Table 2. FIG. 2 shows that when the volume of the powder to be added for the adhesive layer exceeds about 20%, the emission amount of the brilliant blue is raised. Also, FIG. 2 shows that when the volume of the powder to be added for the adhesive layer exceeds about 50%, the emission amount of the brilliant blue reaches a peak.

As a result, when the volume of the powder to be added for the adhesive layer exceeds about 20%, it seems that the spaces (voids) between the powder is beginning to form in the adhesive layer, and the brilliant blue inside the adhesive layer is beginning to be released via the spaces. Also, when the volume of the powder to be added for the adhesive layer exceeds about 50%, it seems that the spaces (voids) between the powder are completely formed in the adhesive layer. Thus, we think that the additional powder makes no change in the release property of the brilliant blue.

On the other hand, it was shown that when the volume of the powder to be added exceeds about 110% of the volume of the adhesive layer, the preparation becomes hard, and the adhesibility of the preparation is deteriorated and it is unsuitable for a drug formulation. Thus, it was demonstrated that the upper limit of the amount of AEROSIL® to be added was about 110%.

Next, CEOLUS® (crystalline cellulose) having a larger bulk density (i.e., having a smaller particle size) than AEROSIL® was used as the powder, and the effects in various volumes of the powder were evaluated. Specifically, the release property of the brilliant blue from the adhesive layer was evaluated using CEOLUS® as the powder according to the above Table 2.

The "volume ratio of the powder to the adhesive layer" was calculated according to the specific gravity of the adhesive layer containing the drug solution defined as 1.

Figure 3:
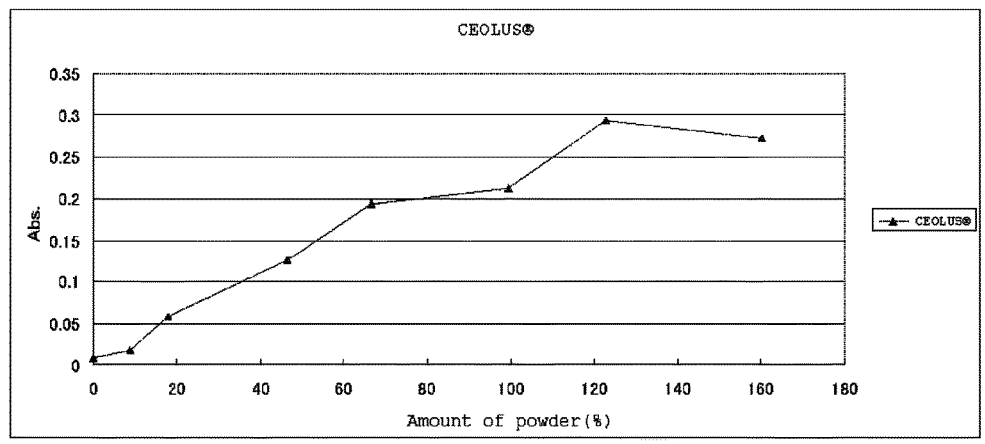
FIG. 3 is a diagram showing the correlation between the emission amount of the blue pigment and the volume ratio of the powder to the plaster base material in a similar measurement method to that of FIG. 2, except that crystalline cellulose is used as the powder.

FIG. 3 is a diagram showing the emission amount of brilliant blue FCF as shown in the above Table 3. FIG. 3 shows that when the volume of CEOLUS® to be added for the adhesive layer exceeds about 20%, the emission amount of brilliant blue is gradually raised. Also, FIG. 3 shows that when the volume of CEOLUS® to be added exceeds about 120% of the volume of the adhesive layer, the emission amount of brilliant blue reaches a peak.

The difference between the amounts (volumes) of the powder to be added as shown in the above Table 2 and Table 3 is shown to be influenced by the difference between the bulk densities of CEOLUS® and AEROSIL®. The bulk density of AEROSIL® is smaller than that of CEOLUS®, and thus the volume of the spaces (voids) between the powder becomes larger. As a result, AEROSIL® in small amount can make the spaces (voids) in the adhesive layer.

Figure 4:
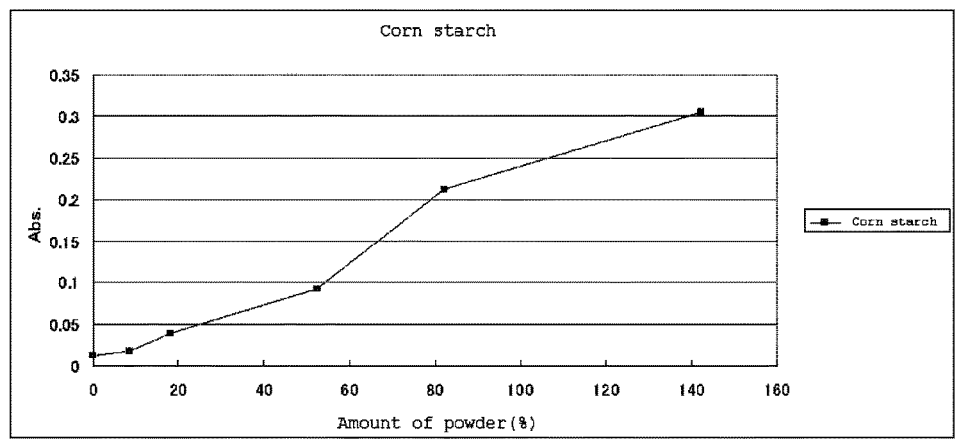
FIG. 4 is a diagram showing the correlation between the emission amount of the blue pigment and the volume ratio of the powder to the plaster base material in a similar measurement method to that of FIG. 2, except that corn starch is used as the powder.

In addition, the results of corn starch having a larger bulk density than CEOLUS® are shown in Table 4 below and FIG. 4.

TABLE 3

|  | B1 | B2 | B3 | B4 | B5 | B6 | B7 | B8 |
|---|---|---|---|---|---|---|---|---|
| Drug Solution: | | | | | | | | |
| Brilliant blue FCF | 0.016 | 0.016 | 0.016 | 0.016 | 0.016 | 0.016 | 0.016 | 0.016 |
| Triethanolamine Levulinate/Macrogol 400 | 10 | 9.88 | 9.76 | 9.39 | 9.15 | 8.78 | 9.53 | 8.17 |
| Adhesive: | | | | | | | | |
| Triethanolamine Levulinate/Macrogol 400 | 10 | 9.88 | 9.76 | 9.39 | 9.15 | 8.78 | 9.53 | 8.17 |
| Terpene Resin | 38 | 37.54 | 37.07 | 35.68 | 34.75 | 33.36 | 32.43 | 31.03 |
| SIS | 20 | 19.76 | 19.51 | 18.78 | 18.29 | 17.56 | 17.07 | 16.33 |
| Liquid Parffin | 17 | 16.79 | 16.59 | 15.96 | 15.55 | 14.92 | 14.51 | 13.88 |
| Butylhydroxytoluene | 1 | 0.99 | 0.98 | 0.98 | 0.97 | 0.96 | 0.95 | 0.94 |
| (Total weight of adhesive layer) | 96.0 | 94.8 | 93.7 | 90.1 | 87.8 | 84.3 | 81.9 | 78.4 |
| Filler (Powder): | | | | | | | | |
| CEOLUS ®(crystalline cellulose) | 0 | 1.17 | 2.35 | 5.87 | 8.21 | 11.73 | 14.08 | 17.6 |
| (Volume) | | (8.4) | (16.8) | (41.9) | (58.6) | (83.8) | (100.5) | (125.7) |
| Volume ratio of powder to adhesive layer (%) | 0 | 8.9 | 17.9 | 46.5 | 66.7 | 99.4 | 122.7 | 160.3 |
| Preparation Form: | good | good | good | good | good | good | good | good |
| Emission Amount (Absorbance/Measurement Wavelength 630 nm) | 0.008 | 0.017 | 0.058 | 0.125 | 0.194 | 0.213 | 0.294 | 0.273 |

[NOTE]
The volume of CEOLUS ® was calculated according to the weight thereof/the bulk density thereof.

TABLE 4

|  | C1 | C2 | C3 | C4 | C5 | C6 | C7 | C8 |
|---|---|---|---|---|---|---|---|---|
| Drug Solution: | | | | | | | | |
| Brilliant blue FCF | 0.016 | 0.016 | 0.016 | 0.016 | 0.016 | 0.016 | 0.016 | 0.016 |
| Triethanolamine Levulinate/Macrogol 400 | 10 | 9.58 | 9.17 | 7.92 | 7.09 | 5.84 | 5.01 | 3.77 |
| Adhesive: | | | | | | | | |
| Triethanolamine Levulinate/Macrogol 400 | 10 | 9.58 | 9.17 | 7.92 | 7.09 | 5.84 | 5.01 | 3.77 |
| Terpene Resin | 38 | 36.42 | 34.84 | 30.10 | 26.94 | 22.21 | 19.05 | 14.31 |
| SIS | 20 | 19.17 | 18.34 | 15.84 | 14.18 | 11.69 | 10.03 | 7.53 |
| Liquid Parffin | 17 | 16.29 | 15.59 | 13.47 | 12.05 | 9.93 | 8.52 | 6.40 |
| Butylhydroxytolene | 1 | 0.96 | 0.92 | 0.79 | 0.71 | 0.58 | 0.50 | 0.38 |
| (Total weight of adhesive layer) | 96.0 | 92.0 | 88.0 | 76.1 | 68.1 | 56.1 | 48.1 | 36.2 |
| Filler (Powder): | | | | | | | | |
| corn starch | 0 | 3.99 | 7.98 | 19.95 | 27.93 | 39.9 | 47.88 | 59.85 |
| (Volume) | | (8.0) | (16.0) | (39.9) | (55.9) | (79.8) | (95.8) | (119.7) |
| Volume ratio of powder to adhesive layer (%) | 0 | 8.7 | 18.2 | 52.4 | 82.1 | 142.2 | 199.2 | 330.7 |
| Preparation Form: | good | good | good | good | good | bad | bad | bad |
| Amount of Emission (Absorbance/Measurement Wavelength 630 nm) | 0.012 | 0.017 | 0.039 | 0.092 | 0.212 | 0.304 | — | — |

[NOTE]
The volume of corn starch was calculated according to the weight thereof/the bulk density thereof.

The "volume ratio of the powder to the adhesive layer" was calculated according to the specific gravity of the adhesive layer containing the drug solution defined as 1. -: not measured because of bad preparations.

In order to make the spaces (voids) between the powder in the adhesive layer by using corn starch having a large bulk density, it was shown that it is necessary to add a large amount of corn starch. However, when corn starch was excessively added, it got difficult to formulate the drug, and thus the measurement of the emission amount of the brilliant blue was discontinued. As a result, the amount of corn starch to be added for maximizing the emission amount of the brilliant blue could not be found.

Figure 5:
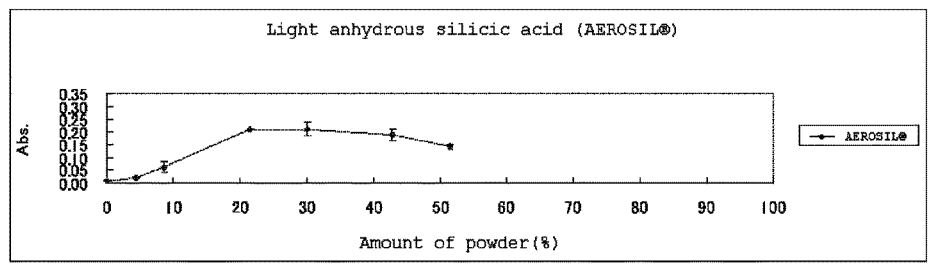
FIG. 5 is a diagram showing the same correlation as that of FIG. 2, but the volume ratio of the powder to the plaster base material is calculated based on the tap density thereof.
Figure 6:
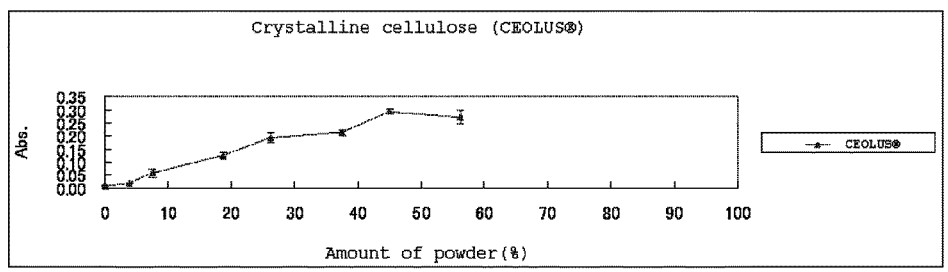
FIG. 6 is a diagram showing the same correlation as that of FIG. 3, but the volume ratio of the powder to the plaster base material is calculated based on the tap density thereof.

Also, when the volume of the powder was calculated based on the tap density of the powder in place of the bulk density of the powder, the calculated volume became smaller. As a result, as shown in FIG. 5 and FIG. 6, the ratio of [the volume of the powder] to [the volume of the adhesive layer] became smaller, and the value in the horizontal axis was decreased.

Thus, the spaces (voids) between the powder formed in the adhesive layer are beginning to be formed by combining the powder when the volume of the powder for the volume of the adhesive layer (comprising a drug, etc.) is about 20% (calculated as the bulk density of the powder) as shown in FIG. 2 and FIG. 3. In addition, as shown in FIG. 5 and FIG. 6, the spaces (voids) between the powder are completely formed when the volume of the powder for the volume of the adhesive layer (comprising a drug, etc.) reached about 60% (calculated as the tap density of the powder). This result is summarized in the following inequality.

$$0.2 \text{ (calculated as the bulk density of powder)} \leq \frac{\text{(the volume of the powder)}}{\text{(the volume of the adhesive layer)}} \leq 0.6$$

(calculated as the tap density of the powder)

More specifically, when the powder is light anhydrous silicic acid, the volume of the powder is preferably in the range of 0.2 to 0.6 calculated as the bulk density thereof, and in the range of 0.1 to 0.3 calculated as the tap density thereof. Similarly, when the powder is crystalline cellulose, the volume of the powder is preferably in the range of 0.2 to 1.2 calculated as the bulk density thereof, and in the range of 0.1 to 0.6 calculated as the tap density thereof. In addition, when the powder is corn starch having a large bulk density, the volume of the powder is preferably in the range of 0.2 to 0.7 calculated as the bulk density thereof, and in the range of 0.1 to 0.4 calculated as the tap density thereof.

Also, when the volume of the powder in the above inequality is converted into the amount (weight) of the powder to be added, the inequality is expressed as the following inequality.

0.2×(the weight of the adhesive layer)×(the bulk density of the powder)≤the amount of the powder to be added≤0.6×(the weight of the adhesive layer)×(the tap density of the powder).

The amount (weight) of the powder to be added can be determined depending on the total weight of the adhesive layer comprising a drug and a solvent. Thus, when the amount of the ingredients such as the drug, the elastomer, and the tackifier in the adhesive layer is maintained at a constant rate, the upper limit and lower limit of the volume of the solvent available for the adhesive layer can be determined. That is, the volume of the solvent to be filled in the spaces (voids) between the powder can be determined. When the volume of the solvent exceeds the upper limit, the solvent exudes onto the surface of the adhesive layer. As a result, the adhesibility of the tape preparation to the skin is decreased, and the tape preparation is easily removed. Thus, the upper limit of the volume of the solvent to be added depends on the amount of the powder to be added.

Example 3

Figure 7:
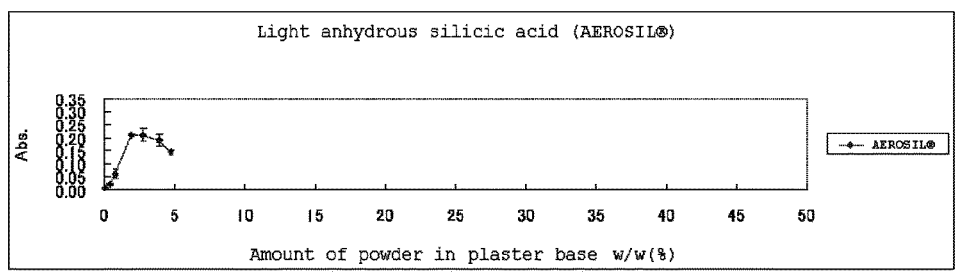
FIG. 7 is a diagram showing the same data as that of FIG. 2 in which the horizontal axis represents the amount of the powder in the adhesive layer of the preparation.
Figure 8:
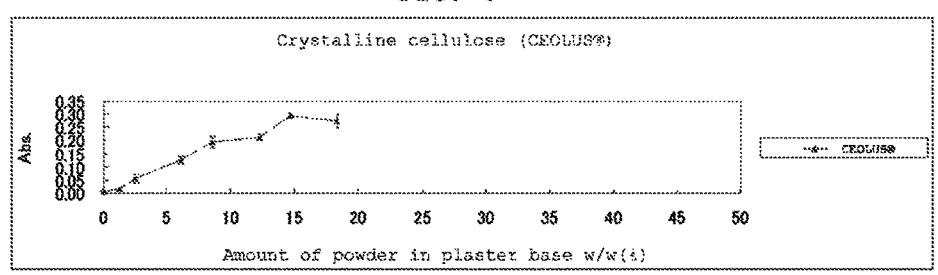
FIG. 8 is a diagram showing the same data as that of FIG. 3 in which the horizontal axis represents the amount of the powder in the adhesive layer of the preparation.
Figure 9:
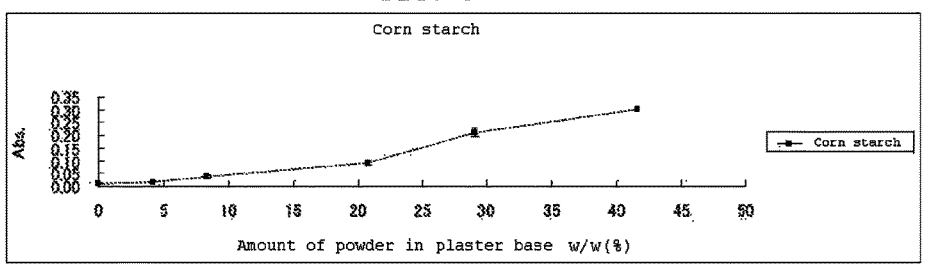
FIG. 9 is a diagram showing the same data as that of FIG. 4 in which the horizontal axis represents the amount of the powder in the adhesive layer of the preparation.

Weight-Composition of Powder and Spaces (Voids) Between Powder Formed in Adhesive Layer (1) Measurement of the Amount of Powder to be Added Required for Forming Spaces (Voids):

The above results of Example 2 were converted to the weight-composition of the powder to show the emission amount of brilliant blue FCF graphically. The results are shown in FIGS. 7 to 9.

The rate of the spaces (voids) between the powder formed in the adhesive layer was estimated based on the weight-composition (w/w %) of the powder, and the estimated rate was shown to be greatly affected by the bulk density (tap density) of the powder. Specifically, it was demonstrated that light anhydrous silicic acid having a large particle size and small bulk density of the powder could form the spaces (voids) between the powder in the adhesive layer in a small amount of light anhydrous silicic acid, whereas crystalline cellulose and corn starch were required to further increase the amount of the powder to be added, and the spaces (voids) between the powder could not be sufficiently formed when the weight-composition of the powder (w/w %) was not high. That is, when the amount of powder having a large particle size such as light anhydrous silicic acid was 1 w/w % or more, the spaces (voids) were beginning to be formed, and when the amount was 2.5 w/w % or more, the spaces (voids) were sufficiently formed. Also, it was shown that the amount of the powder to be added is preferably 5 w/w % or less in view of the emission amount of the brilliant blue.

In addition, when the amount of crystalline cellulose to be added was 2.5 w/w % or more, the spaces (voids) between the powders were beginning to be formed, and when the amount was 15 w/w %, the spaces (voids) between the powders were sufficiently formed. Also, it was shown that the amount of the powder to be added is preferably 18 w/w % or less in view of the emission of the brilliant blue.

Thus, it was demonstrated that the amount of the powder to be added varies depending on the type of the powder to be added, but the preferred amount of the powder is in the range of 1 to 18 w/w %. Also, the amount of light anhydrous silicic acid for forming sufficient spaces (voids) is preferably 1 to 5 w/w %, and more preferably 2.5 to 5 w/w %. Also, it was shown that the amount of crystalline cellulose is preferably 2.5 to 18 w/w %, and more preferably 5 to 15 w/w %.

(2) Measurement of the Amount of Solvent Required for Filling the Spaces (Voids) Formed:

Maintaining the amount of the powder in the adhesive layer (lipophilic adhesive plaster base) at a constant rate and using various solvents, we studied how volume of each solvent is suitable for exuding onto the surface of the adhesive layer without being held in the spaces (voids) between the powder. When a solvent exudes on the surface of the adhesive layer, the adhesibility of the adhesive layer is decreased. Thus, the adhesibility of the surface of the adhesive layer was evaluated to calculate the volume of a solvent held in the spaces (voids) between the powder.

Each reagent was weighted according to the composition (w/w %) in Table 5 below, terpene resin, styrene-isoprene-styrene copolymer (SIS), diethyl sebacate, and liquid paraffin were dissolved in toluene following the conventional solvent method, and then macrogol 400 and light anhydrous silicic acid (AEROZIL® 200) were added thereto and mixed. Then, each mixture was applied on the silicone-coated PET film and dried. After removal of the toluene, the backing support was laminated to prepare each preparation. The ball tack test was performed on the samples to check whether Ball No. 4 was stopped.

The result is shown in Table 5 below.

TABLE 5

|  |  | Formulation | | |
| --- | --- | --- | --- | --- |
|  |  | D1 | D2 | D3 |
| Solvent | Macrogol 400 | 34 | 41 | 45 |
|  | (the volume of the solvent) | (30.6) | (36.9) | (40.5) |
| Adhesive Layer | Terpene Resin | 20 | 20 | 20 |
|  | Styrene-Isoprene-Styrene Copolymer | 15 | 15 | 15 |
|  | Liquid Paraffin | 25 | 18 | 14 |
|  |  | 3 | 3 | 3 |
| Powder | Light Anhydrous Silicic Acid (AEROSIL® 200) | 3 | 3 | 3 |
|  |  | (33.3) | (33.3) | (33.3) |
| Total |  | 100 | 100 | 100 |
| Ratio of the solvent (the drug solution) to the volume of the powder (the amount of the powder/the tap density of the powder) |  | 0.9 | 1.1 | 1.2 |
| Ball Tack Test Result on Ball No. 4 |  | Stopped | Stopped | Not Stopped |

[NOTE]
Macrogol 400: specific gravity of 1.11

The "Drug approval and licensing procedures in Japan" describes that patch preparations have an excellent adhesibility when stopping ball No. 4. As shown in the above Table 5, in the ball tack test of Formulation No. D3, ball No. 4 was not stopped. As a result, the adhesibility of the preparation was deteriorated. The results show that when the solvent (macrogol) exceeds 1.2 times the volume of the powder, the volume of the solvent used exceeds the volume capacity of the spaces (voids) between the powder, and the solvent exudes onto the surface of the adhesive layer.

According to the above results of the ball tack test, it was demonstrated that the volume of the spaces (voids) between the powder in the adhesive layer (lipophilic plaster base material) is smaller than 1.2 times the volume of the powder, and the volume is in the range of about 1.1 times the volume of the powder. As a result, the upper limit of the amount of the solvent to be added can be determined according to the following inequality.

$$\frac{\text{the amount of the solvent to be added}}{(\text{the volume of the solvent to be added})} < \frac{\frac{\text{the amount of the powder to be added}}{\text{the tap density of the powder}}}{(\text{the volume of the powder to be added})} \times 1.2$$

The solvent held in the spaces (voids) in the adhesive layer is a solvent which is hard to dissolve in the adhesive layer (lipophilic plaster base material) (i.e. a solvent which is less compatible with the adhesive layer), and examples of the solvent include an alcohol solvent (e.g. macrogol, propylene glycol, and polyethylene glycol) and a protic solvent such as a fatty acid-based ionic liquid and a fatty acid. On the other hand, an ester solvent (e.g. diethyl sebacate and isopropyl myristate) is more compatible with the adhesive layer (lipophilic plaster base material), and thus it seems that the solvent is hard to be retained in the spaces (voids) in the adhesive layer.

Example 4

Preparation of Tape Preparations Containing Light Anhydrous Silicic Acid

Following the above results of Example 3, tape preparations comprising the powder and agomelatine as an active ingredient were prepared. Each reagent was weighed according to the composition (w/w %) in Table 6 below to prepare the tape preparations by the conventional solvent method. Table 6 also shows the results on the permeability of agomelatine in the Franz cell method.

TABLE 6

|  | Test No. | | | | | | |
| --- | --- | --- | --- | --- | --- | --- | --- |
|  | A068 | A103 | A102 | A092 | A093 | A097 | A098 |
| Agomelatine (Powder) | 1.0 | 1.0 | 1.0 | 1.0 | 1.0 | 1.0 | 1.0 |
| Light Anhydrous Silicic Acid (Organic Solvent) |  | 1.0 | 2.0 | 3.0 | 3.5 | 4.0 | 5.0 |
| Isopropyl Myristate | 5.0 | 5.0 | 5.0 | 5.0 | 5.0 | 5.0 | 5.0 |
| Propyl Carbonate | 5.0 | 5.0 | 5.0 | 5.0 | 5.0 | 5.0 | 5.0 |
| Polyethylene Glycol | 5.0 | 5.0 | 5.0 | 5.0 | 5.0 | 5.0 | 5.0 |
| N-Methyl-Pyrrolidone (Fatty Acid-Based Ionic Liquid) | 2.8 | 2.8 | 2.8 | 2.8 | 2.8 | 2.8 | 2.8 |
| Triisopropanolamine Decanoate | 0.9 | 0.9 | 0.9 | 0.9 | 0.9 | 0.9 | 0.9 |
| Diisopropanolamine Oleate | 1.3 | 1.3 | 1.3 | 1.3 | 1.3 | 1.3 | 1.3 |
| Diisopropanolamine Isostearate | 3.0 | 3.0 | 3.0 | 3.0 | 3.0 | 3.0 | 3.0 |
| Triethanolamine Lactate (Lipophilic plaster base) | 2.0 | 2.0 | 2.0 | 2.0 | 2.0 | 2.0 | 2.0 |
| Terpene Resin | 38.0 | 38.0 | 37.0 | 36.0 | 36.0 | 36.5 | 36.0 |
| SIS | 18.0 | 17.0 | 17.0 | 17.0 | 17.0 | 16.0 | 16.0 |
| Liquid Paraffin (Antioxidant) | 17.0 | 17.0 | 17.0 | 17.0 | 16.5 | 16.5 | 16.0 |
| Butylhydroxytoluene | 1.0 | 1.0 | 1.0 | 1.0 | 1.0 | 1.0 | 1.0 |
| Total | 100.0 | 100.0 | 100.0 | 100.0 | 100.0 | 100.0 | 100.0 |
| Skin Permeation Amount (μg/cm²/6 hr) | 51.7 | 19.1 | 17.2 | 12.8 | 7.1 | 9.4 | 5.0 |

As shown in the above Table 6, the release property of the drug in the tape preparations containing light anhydrous silicic acid had a tendency to be sustainedly released with increasing the amount of the powder, and the cumulative skin permeation amount for 6 hours tended to be decreased. Then, we changed the powder from light anhydrous silicic acid to crystalline cellulose to evaluate the changes in the release property of the drug.

Example 5

Preparation of Tape Preparations Containing Crystalline Cellulose

In the same manner as Example 4, tape preparations containing crystalline cellulose as the powder were prepared. Each reagent was weighed according to the composition (w/w %) in Table 7 below to prepare the tape preparations by the conventional solvent method. Table 7 also shows the results about the permeability of agomelatine in the Franz cell method.

TABLE 7

|  | Test No. | | | | | |
| --- | --- | --- | --- | --- | --- | --- |
|  | A068 | A104 | A105 | A106 | A107 | A108 |
| Agomelatine (Powder) | 1.0 | 1.0 | 1.0 | 1.0 | 1.0 | 1.0 |
| Crystalline Cellulose (Organic Solvent) |  | 1.0 | 2.0 | 3.0 | 4.0 | 5.0 |
| Isopropyl Myristate | 5.0 | 5.0 | 5.0 | 5.0 | 5.0 | 5.0 |
| Propyl Carbonate | 5.0 | 5.0 | 5.0 | 5.0 | 5.0 | 5.0 |
| Polyethylene Glycol | 5.0 | 5.0 | 5.0 | 5.0 | 5.0 | 5.0 |
| N-Methyl-Pyrrolidone (Fatty Acid-Based Ionic Liquid) | 2.8 | 2.8 | 2.8 | 2.8 | 2.8 | 2.8 |
| Triisopropanolamine Decanoate | 0.9 | 0.9 | 0.9 | 0.9 | 0.9 | 0.9 |
| Diisopropanolamine Oleate | 1.3 | 1.3 | 1.3 | 1.3 | 1.3 | 1.3 |
| Diisopropanolamine Isostearate | 3.0 | 3.0 | 3.0 | 3.0 | 3.0 | 3.0 |
| Triethanolamine Lactate (Lipophilic plaster base) | 2.0 | 2.0 | 2.0 | 2.0 | 2.0 | 2.0 |
| Terpene Resin | 38.0 | 38.0 | 37.0 | 36.0 | 36.0 | 35.0 |
| SIS | 18.0 | 17.0 | 17.0 | 17.0 | 16.5 | 16.5 |
| Liquid Paraffin (Antioxidant) | 17.0 | 17.0 | 17.0 | 17.0 | 16.5 | 16.5 |
| Butylhydroxytoluene | 1.0 | 1.0 | 1.0 | 1.0 | 1.0 | 1.0 |
| Total | 100.0 | 100.0 | 100.0 | 100.0 | 100.0 | 100.0 |
| Skin Permeation Amount (μg/cm²/6 hr) | 51.7 | 9.4 | 8.1 | 6.9 | 4.9 | 6.6 |

As shown in the above Table 7, the drug in the tape preparations containing crystalline cellulose was more sustainedly released as compared to the drug in the tape preparation containing light anhydrous silicic acid, and thus the cumulative skin permeation amount for 6 hours was also more decreased.

The results suggest that the spaces (voids) between the powder were not sufficiently formed in the adhesive layer due to the small amount of crystalline cellulose to be added. Specifically, it seemed that it is necessary to increase the bulk density of the powder to suitably form the spaces (voids) between the powder. Thus, we tried mixing some types of powders having different particle sizes to improve the bulk density of the powder.

Figure 10:
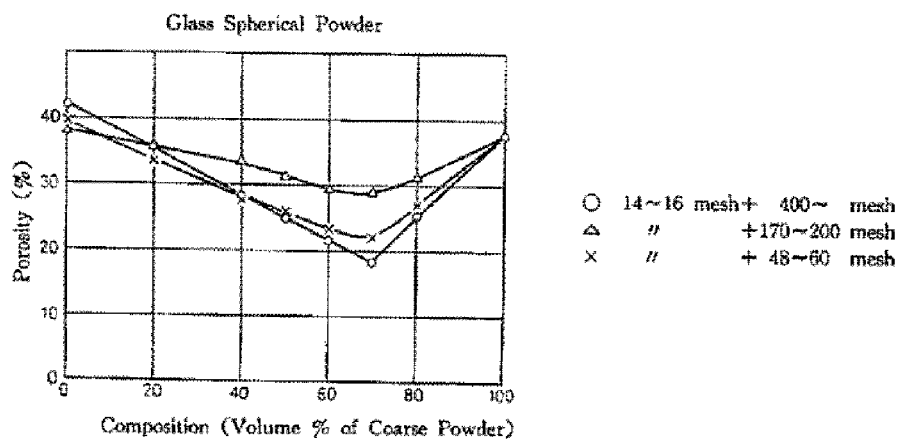
FIG. 10 is a diagram showing that when two types of powders having different particle sizes are combined and the volume of powder having a larger particle size accounts for about 70% of the total, the volume of the mixture of the powders becomes the smallest.

It has been known that the volume of a mixture of powders becomes the smallest when two types of powders having different particle sizes are combined and the amount of powder having a larger particle size to be added accounts for about 70% of the total as shown in FIG. 10 (e.g. Kimio KAWAKITA et al., *Bulletin of the Faculty of Engineering*, Hosei University 2, pages 47-53). Thus, we studied about the combination of powders and the release property of the drug based on the above composition.

Example 6

Preparation of Tape Preparation Containing Light Anhydrous Silicic Acid and Crystalline Cellulose Light anhydrous silicic acid (having a larger particle size) and crystalline cellulose (having a smaller particle size) were used as the powder having different particle sizes to prepare tape preparations containing powder according to the composition (w/w %) in Table 8 below. Table 8 also shows the results about the permeability of agomelatine in the Franz cell method.

TABLE 8

|  | Test No. | | | |
| --- | --- | --- | --- | --- |
|  | A068 | A082 | A085 | A088 |
| Agomelatine (Powder) | 1.0 | 1.0 | 1.0 | 1.0 |
| Light Anhydrous Silicic Acid |  | 3.0 | 2.0 | 1.0 |
| Crystalline Cellulose (Organic Solvent) |  | 3.0 | 3.0 | 3.0 |
| Isopropyl Myristate | 5.0 | 5.0 | 5.0 | 5.0 |
| Propyl Carbonate | 5.0 | 4.0 | 4.0 | 4.5 |
| Polyethylene Glycol | 5.0 | 4.0 | 4.0 | 4.5 |
| N-Methyl-Pyrrolidone (Fatty Acid-Based Ionic Liquid) | 2.8 |  | 0.8 | 0.8 |
| Triisopropanolamine Decanoate | 0.9 | 0.9 | 0.9 | 0.9 |
| Diisopropanolamine Oleate | 1.3 | 1.3 | 1.3 | 1.3 |
| Diisopropanolamine Isostearate | 3.0 | 3.0 | 3.0 | 3.0 |
| Triethanolamine Lactate (Lipophilic plaster base) | 2.0 | 2.0 | 2.0 | 2.0 |
| Terpene Resin | 38.0 | 36.0 | 35.0 | 35.0 |
| SIS | 18.0 | 17.0 | 17.0 | 17.0 |
| Liquid Paraffin | 17.0 | 17.8 | 19.0 | 19.0 |
| Polybutene (Antioxidant) |  | 1.0 | 1.0 | 1.0 |
| Butylhydroxytoluene | 1.0 | 1.0 | 1.0 | 1.0 |
| Total | 100.0 | 100.0 | 100.0 | 100.0 |
| Skin Permeation Amount ($\mu g/cm^2/6$ hr) | 51.7 | 12.2 | 11.7 | 45.1 |

As shown in the above Table d, when light anhydrous silicic acid (having a larger particle size) and crystalline cellulose (having a smaller particle size) were combined at a weight ratio of 1:3, the release property of the drug was unexpectedly and drastically improved. The result was obtained when the amount of light anhydrous silicic acid having a larger particle size was 25%. FIG. 10 shows that the bulk density of the mixture can reach a peak when the amount of light anhydrous silicic acid to be added is 70%. However, the result was against the theory, which showed that 70 to 80% crystalline cellulose was necessary to suitably form the spaces (voids) in the adhesive layer between the mixed powders. As described above, it was found that it is preferable in case of mixed powders to mix powder having a smaller particle size and powder having a larger particle size at a ratio of 70 to 80:20 to 30 to effectively form the spaces (voids) in the adhesive layer. As a result, the drug solution can be retained in the spaces (voids) of the adhesive layer or the drug solution can be transferred to the surface of the tape preparation via the spaces (voids), and thus the drug solution or the drug can be released from the surface of the tape preparation.

Example 7

Evaluation of the Release Property of Drug with Adhesive Layer Containing Powder The above results of Example 6 suggest that when two types of powders (fillers) having different particle sizes are added into the adhesive layer of the tape preparations, the drug solution containing the drug (agomelatine) can be retained in the spaces (voids) between the powder (filler) or between the powder and the adhesive layer, and also the drug solution or the drug within the adhesive layer can be effectively released onto the surface of the adhesive layer via the spaces. As a result, it was shown that the ratio of the residual drug in the adhesive layer was much lower than that of the conventional tape preparations.

The tape preparations were prepared according to the composition (w/w %) in Table 9 below, and the change in the drug blood level in mice was measured to verify the above effect of the present invention. Specifically, the tape preparations were prepared according to the method of Example 2. The tape preparations were used for evaluating the transdermal absorbability of the drug in the Franz cell method of Test Example 1 and the change in the drug blood level in mice. The results are shown in Table 9 and FIG. 11.

TABLE 9

|  | Test No. | |
| --- | --- | --- |
|  | A260 | A244 |
| Agomelatine (Powder) | 2.0 | 2.0 |
| Crystalline Cellulose |  | 3.0 |
| Light Anhydrous Silicic Acid (Organic Solvent) |  | 1.0 |
| Dimethylisosorbide | 1.2 | 1.2 |
| Isopropyl Myristate | 5.7 | 5.7 |
| Propyl Carbonate | 5.0 | 5.0 |
| Polyethylene Glycol (Fatty Acid-Based Ionic Liquid) | 7.5 | 7.5 |
| Triethanolamine Isostearate | 2.5 | 2.5 |
| Triethanolamine Lactate (Lipophilic plaster base) | 1.5 | 1.5 |
| SIS | 17.2 | 16.5 |
| Terpene Resin | 35.0 | 33.7 |
| Liquid Paraffin (Other Additives) | 19.5 | 17.5 |
| Butylhydroxytoluene | 1.0 | 1.0 |
| Total | 100.0 | 100.0 |
| Cumulative Skin Permeation Amount at 6 hours ($\mu g/cm^2$) | 6.2 | 36.5 |

As shown in Table 9, comparing the preparation of Test No. A260 of having the adhesive layer with no powder with the preparation of Test No. A244 having the adhesive layer containing the powders, the transdermal absorbability of the drug in the tape preparation containing the powders was dramatically improved. Specifically, it was shown that the transdermal absorbability of the drug in the preparation containing the powders was improved by about 6 times as compared to that of the tape preparation with no powder.

This means that the release of the drug from the adhesive layer was increased by about 6 times. Thus, it seems that the drug was easily released from the surface of the adhesive layer via the spaces (voids) formed by the addition of the powders to the adhesive layer.

Figure 11:
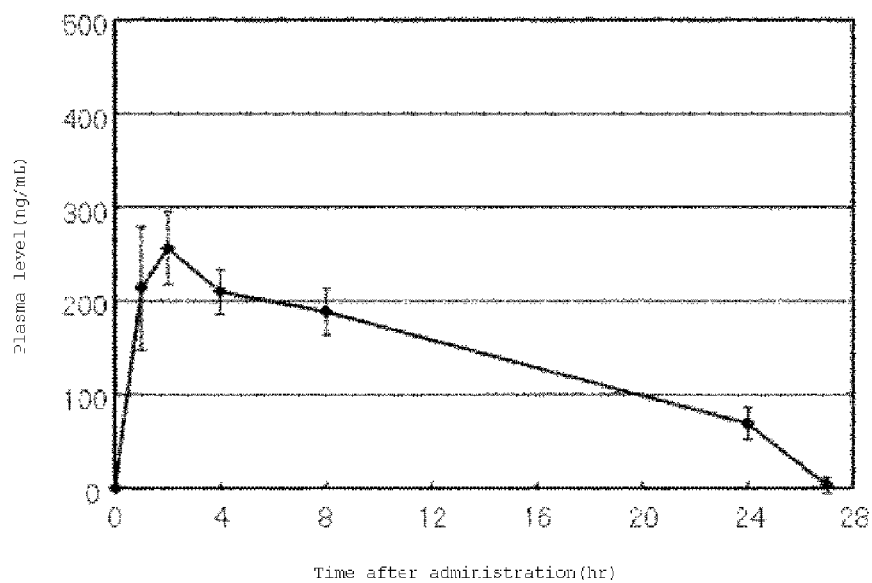
FIG. 11 is a diagram showing in vivo blood level change of the drug in mice produced by the use of the tape preparation containing powders (Test No. A244).

In addition, it has been found that when in vivo drug blood level in mice was evaluated according to Test Example 1, the preparation containing the powders (Test No. A244) sustainedly released the drug as shown in FIG. 11.

Figure 12:
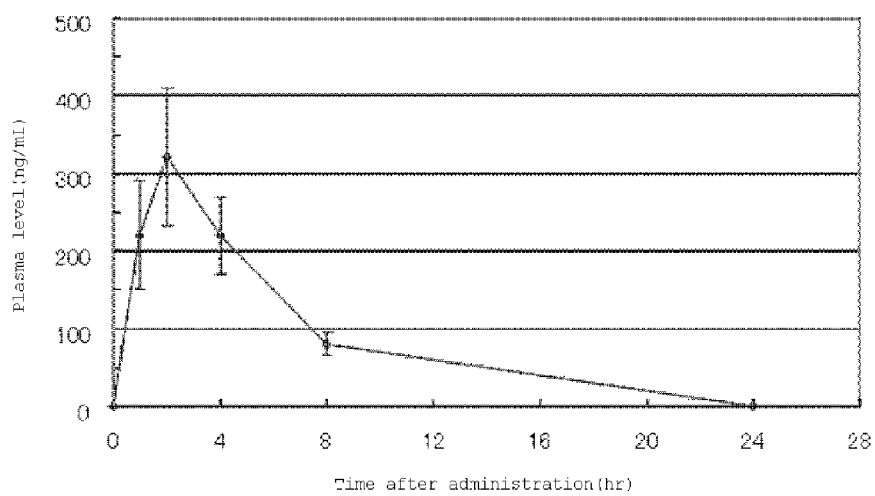
FIG. 12 is a diagram showing the change in the drug blood level in mice produced by the use of the tape preparation with no powder (Test No. A068).

The preparation of Example 6 with no powder (Test No. A068) was shown to have the excellent transdermal absorbability of the drug. As shown in FIG. 12, however, the change in the drug blood level was evaluated with a rat treated with (Test No. A068), in which the drug blood level reached a peak 2 hours after the preparation was applied to the skin, and then was rapidly decreased. The change in the drug blood level as shown in FIG. 12 is greatly different from that of the present invention as shown in FIG. 11.

Figure 14:
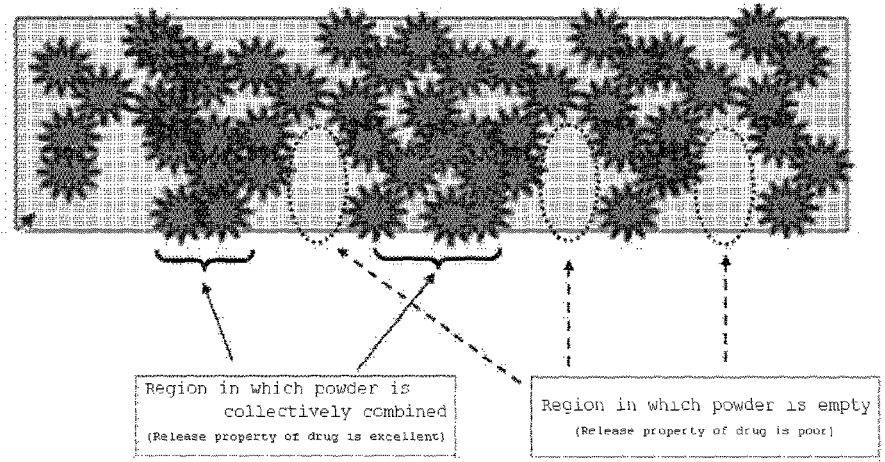
FIG. 14 is a conceptual diagram showing the imbalance of the powder in the adhesive layer which is presumed to produce biphasic behaviors as shown in FIG. 13. The result means the presence of the region forming the spaces (voids) in which the powder is collectively combined in the adhesive layer and the region in which the powder is relatively empty in the adhesive layer, that is, the region in which the spaces (voids) are not sufficiently formed.

FIG. 13 shows that the change in the drug blood level of the present invention as shown in FIG. 11 is composed of biphasic behaviors of a dashed part showing immediate-release property of the drug and a dotted part showing the slow-release property of the drug. As shown in FIG. 14, these behaviors are derived from the presence of the region forming the spaces (voids) in which the powders are collectively combined in the adhesive layer and the region in which the powder is relatively empty in the adhesive layer, that is, the region in which the spaces (voids) are not sufficiently formed.

As described above, the release property of the drug from the adhesive layer containing the powder of the present invention is composed of the biphasic properties (immediate-release and sustained-release properties) as shown in FIG. 13. Thus, it has been found that it is possible to make any one selected from the immediate-release and sustained-release behaviors of the drug better by arranging the amount of the powders to be added and the combination of the powders.

Example 9

Evaluation of the Utilization Rate of Drug in Tape Preparations with Adhesive Layer Containing Powder (1) Tape Preparation Comprising Agomelatine as Active Ingredient In the same manner as Example 2, each reagent was weighed according to the composition (part by weight) in Table 10 below to prepare the tape preparations comprising agomelatine as a drug.

Specifically, agomelatine was mixed with the fatty acid-based ionic liquids to prepare a drug solution. Following the conventional solvent method using toluene as the solvent, the organic solvents, the antioxidants, the lipophilic plaster base materials, and the drug solution were mixed. Next, crystalline cellulose and light anhydrous silicic acid were added thereto and mixed, and then the mixture was applied on the silicone-coated PET film and dried. After removal of the toluene, the backing support was laminated to prepare the preparation.

Following Test Example 1 below, the in vitro skin permeability test was performed with the prepared patch preparations comprising agomelatine. The results are also shown in Table 10.

TABLE 10

|  | Test No. | |
|---|---|---|
|  | A223 | A197 |
| Agomelatine (Powder) | 1.0 | 1.0 |
| Light Anhydrous Silicic Acid |  | 1.0 |
| Crystalline Cellulose |  | 3.0 |
| (Organic Solvent) |  |  |
| Isopropyl Myristate | 3.8 | 3.8 |
| Propyl Carbonate | 6.0 | 5.0 |
| Polyethylene Glycol | 6.0 | 5.0 |
| (Fatty Acid-Based Ionic Liquid) |  |  |
| Triethanolamine Isostearate | 2.5 | 2.5 |
| Triethanolamine Lactate | 1.5 | 1.5 |
| (Lipophilic plaster base) |  |  |
| Terpene Resin | 36.3 | 35.3 |
| Styrene-Isoprene-Styrene Block Copolymer | 20.0 | 19.0 |
| Liquid Paraffin | 19.5 | 19.5 |
| (Other Additives) |  |  |
| Kollidon ® K90 | 0.5 | 0.5 |
| Oleic Acid | 1.9 | 1.9 |
| Butylhydroxytoluene | 1.0 | 1.0 |
| Total |  |  |
| Skin Permeation Amount ($\mu g/cm^2/6$ hr) | 9.1 | 26.7 |

As shown in Test Nos. A197 and A223 of the above Table 10, the transdermal absorbability of agomelatine in the tape preparation containing the powders was improved by about 3 times.

In addition, the measured ratio of the residual drug in the preparation of Test No. A197 was about 40%. As a result, it was found that the ratio of trandermally-absorbed agomelatine was about 60%. Thus, it was shown that the tape preparation of the present invention containing powder produced the excellent effect that the drug was transdermally absorbed at a high utilization rate.

(2) Tape Preparations Comprising Oxycodone as Active Ingredient

In the same manner as Example 2, each reagent was weighed according to the composition (part by weight) in Table 11 below to prepare the tape preparations comprising oxycodone as a drug.

Specifically, oxycodone hydrochloride hydrate was mixed with the fatty acid-based ionic liquids to prepare a drug solution. Following the conventional solvent method using toluene as the solvent, organic solvents, antioxidants, lipophilic plaster base materials, light anhydrous silicic acid, and the drug solution were mixed, and then each mixture was applied on the silicone-coated PET film and dried. After removal of the toluene, the backing support was laminated to prepare the preparations.

Following Test Example 1 below, the in vitro skin permeability test was performed with the prepared patch preparations comprising oxycodone. The results are also shown in Table 11.

TABLE 11

| | Test No. | | |
|---|---|---|---|
| | K886 | K884 | N423 |
| Oxycodone Hydrochloride Hydrate (Powder) | 2.31 | 2.31 | 2.31 |
| Light Anhydrous Silicic Acid (Organic Solvent) | | 4.0 | 4.0 |
| Isopropyl Myristate | 5.0 | 5.0 | 5.0 |
| Propyl Carbonate | 10.0 | 10.0 | 10.0 |
| Propylene Glycol | 14.5 | 14.5 | |
| Dipropylene Glycol | | | 5.0 |
| Oleyl Alcohol | | | 5.0 |
| Diethyl Sebacate (Fatty Acid-Based Ionic Liquid + Fatty Acid) | | | 7.0 |
| Capric Acid | 0.98 | 0.98 | 0.98 |
| Isostearic Acid | 6.0 | 6.0 | 6.0 |
| Myristic Acid | 0.4 | 0.4 | 0.4 |
| Oleic Acid | 0.8 | 0.8 | 0.8 |
| Diisopropanolamine (Lipophilic plaster base) | 1.65 | 1.65 | 1.98 |
| Terpene Resin | 27.0 | 27.0 | 30.0 |
| Plastibase ® | 5.0 | 5.0 | |
| Styrene-Isoprene-Styrene Block Copolymer | 15.0 | 15.0 | 16.0 |
| Liquid Paraffin (Other Additives) | 3.27 | 3.27 | 4.54 |
| Butylhydroxytoluene | 1.0 | 1.0 | 1.0 |
| Ascorbic Acid | 0.1 | 0.1 | 0.1 |
| Sodium Lactate | | | 0.9 |
| Total | 96.0 | 100.0 | 100.0 |
| Skin Permeation Amount (μg/cm²/6 hr) | 122 | 160 | 89 |
| Adhesibility Test (Ball Tack Test) | 2 | 37 | — |
| Adhesion Time of Ball No. 4 (sec) | (difficulty in stopping) | (stopping) | |
| Ratio of the residual drug (%) | — | 15 | 19 |

[NOTE]
—: Not measured

As shown in the above Table 11, the tape preparation with no powder (Test No. K886) contains a large volume of the solvent, and thus the solvent exudes onto the surface of the adhesive layer. As a result, the adhesibility of the tape preparation is not strong. On the other hand, the preparation containing the powder (Test No. K884) which has the same composition as the tape preparation with no powder (Test No. K886) was improved in the transdermal absorbability of the drug by 1.3 times. And, the adhesibility of the tape preparation was also increased. In addition, the ratio of the residual drug in the tape preparation containing the powder was about 15%, and thus it is presumed that the ratio of the transdermally-absorbed drug was about 85%.

As described above, the composition for the tape preparation containing the powder was improved in the transdermal absorbability of the drug, and the utilization rate of the drug was dramatically improved. The utilization rate of the drug in conventional tape preparations is generally about 10%, whereas the utilization rate of the drug in the tape preparations containing the powder (Test No. K884 and Test No. N423) was more than 80%, said high utilization rate of the drug was an excellent result. In addition, it was shown that the adhesibility of the tape preparations containing the powder was also effectively maintained by comparison of the preparations of Test No. K886 and Test No. 884.

The preparation of Test No. N423 is a tape preparation in which the amount of the powder to be added is decreased and the relative amount of the ester solvent is increased as compared to the preparation of Test No. K884. On the other hand, the skin permeation amount of the preparation of Test No. N423 in Table 11 was decreased by about half as compared to that of the preparation of Test No. K884, but the ratio of the residual drug was 19%, i.e., the ratio of the residual drug showed little change. The drug blood level was measured according to Test Example 2. The result showed that the drug blood level reached a peak about 3 hours after the preparation was applied to the skin as shown in Table 12 below and FIG. 15.

TABLE 12

| | 0 hr | 3 hr | 8 hr | 24 hr |
|---|---|---|---|---|
| Drug Blood level (ng/mL) | 0 | 54.5 | 16.5 | 0 |
| Ratio of the residual drug (%) | | | 19 | |

The volume of the powder in the preparation of Test No. N423 (33.3 ml in 100 g of the preparation) is thought to be close to that of the solvent which is less compatible with the powder such as an alcohol solvent and a fatty acid-based ionic liquid. From the result, we think that oxycodone can be easily released as shown in Table 12 and FIG. 15. Thus, the image in FIG. 14 is supported by the change in the drug blood level.

Test Example 1

In Vitro Skin Permeability Test

The tests for evaluating the transdermal absorbability of agomelatine in the tape preparations of Examples 4 to 9 were performed using a Franz diffusion cell (the permeable area: 1 cm², the volume of the receptor solution: 8 mL) at a test temperature of 32° C. as follows:
(1) Rat's skin: skin isolated from the abdomen of a 5-week old Wistar rat (male)
(2) Receptor solution: physiological saline+10% ethanol
(3) Concentration measurement of the permeable drug: HPLC The commercially available rat's abdominal frozen skin (5-week old Wistar rat) was mounted in a vertical diffusion cell (the effective diffusion area: 1 cm²). Each sample in Tables 5 to 11 was applied to the stratum corneum side, and physiological saline+10% ethanol was applied to the dermic layer side. The skin permeability of the drug was measured by HPLC to determine the cumulative permeation amount of the drug for 2 hours and 4 hours. As a result, the transdermal absorbability of agomelatine as shown in Tables 5 to 11 could be evaluated.

Test Example 2

Test for Evaluating In Vivo Drug Blood Levels in Rats (1) Laboratory Animal:
  5-week old Wistar rat (male)
(2) Test Method:
  The test sample was prepared by cutting the preparation sample of Test No. A068 (agomelatine, 133 μg/cm²) into 2 cm×2 cm as an adhesive plaster type patch preparation. One group was composed of 6 rats. The hairs around the administration site (from the back to the lateral region) on the rats were removed with an electric hair clipper [THRIVE, Model 5500 (0.05 mm), Daito Electric Machine Industry Co., Ltd.], and then the whiskers on the rats was removed with an electric shaver (Cleancut, Seiko S-Yard Co. Ltd.). To each rat were attached 3 sheets of the preparation samples, and blood was collected from the rats 1 hour, 2 hours, 4 hours, 8 hours, 12 hours, and 24 hours after administration.

To glass tubes were added 200 μl of the blood plasma collected from the rats, and 200 μl of physiological saline was added thereto and the plasma was homogenized. Then, 500 μl of diethyl ether was added thereto, and each mixture was stirred with a vortex mixer, and then centrifuged for 10 minutes to collect the ether layer. Similar ether extraction method was performed on the remaining water layer 3 times in total. The extracted ether layer was combined, and the solvent in the combined ether layer was distilled away under high purity nitrogen stream. After evaporation of the ether, 200 μl of water was added to the resulting dried residues to dissolve the residues. Then, each solution was passed through a 0.45 μm filter for filtration, and 10 μl of the filtrate was analyzed by HPLC.

Also, the preparation sample of Test No. A244 (agomelatine, 266 μg/cm$^2$) was prepared to measure the drug blood levels in the rats in the same manner as the above.

As with the above, using oxycodone, the drug blood levels in the rats were measured (oxycodone hydrochloride, 286 μg/cm$^2$). The preparation of Test No. N423 was used as the sample.

(3) Results

Figure 15:
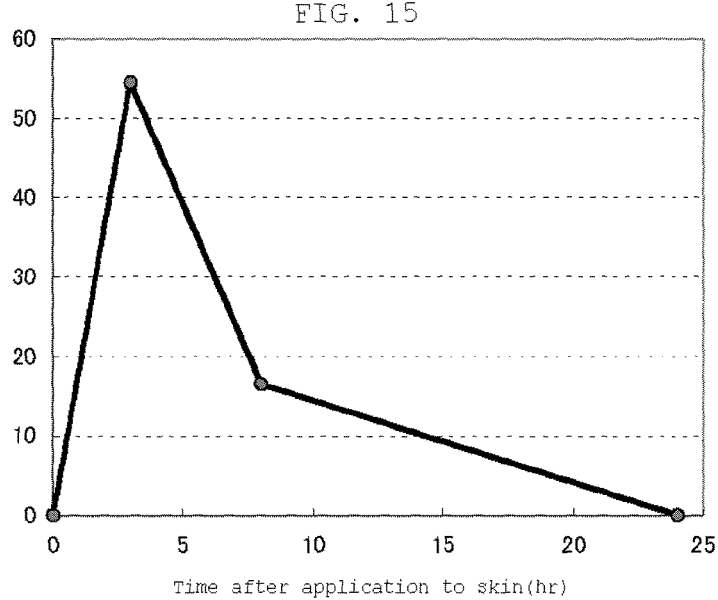
FIG. 15 is a diagram showing the change in the drug blood level over time in the rat produced by the use of the preparation of Test No. N423. The sample of the present invention mainly produces the immediate-release property of the drug.

FIG. 11 and FIG. 12 show the changes in the level of agomelatine in the plasma obtained from the above analyzed results. In addition, FIG. 15 shows the change in the level of oxycodone in the plasma.

INDUSTRIAL APPLICABILITY

The non-aqueous tape preparation of the present invention comprising powder ingredient is characterized in that the powder ingredient makes spaces in a lipophilic adhesive layer, a drug solution is retained in the spaces, and then a drug is gradually released. Also, the tape preparation has an improved adhesibility since a solvent is not retained onto the surface of the adhesive layer of the tape preparation. In addition, both of the adhesibility of the tape preparation and the release property of the drug solution, which are conflicting factors in normal tape preparations, can be improved in the present invention, and thus the transdermal absorbability of the drug can also be improved. Thus, the tape preparation of the present invention has an excellent adhesibility to the skin and further an improved transdermal absorbability of the drug, based on the above effects. Also, the tape preparation can sustainedly release the drug since the drug solution is gradually released from the spaces between the powder. As a result, the non-aqueous tape preparation of the present invention has made it possible to expand the use to new applications in the tape preparation comprising a drug solution in which a drug is dissolved in an organic solvent with high polarity or the non-aqueous tape preparation comprising an ionic liquid, and thus has also made it possible to expand the possibility of treating diseases with the tape preparation.

The invention claimed is:

1. A composition for a non-aqueous patch preparation comprising a drug with hydrophilic residues,
an organic solvent, and
an anhydrous silicic acid powder present in a concentration from 1.9% by weight to 3.8% by weight of the composition, wherein
the powder for an adhesive layer is contained as shown in the following inequality:

0.2×(the weight of the adhesive layer)×(the bulk density of the powder)≤the amount of the powder to be added≤0.6×(the weight of the adhesive layer)×(the tap density of the powder).

2. The composition according to claim 1, wherein the organic solvent comprises a fatty acid-based ionic liquid and/or a salicylic acid-based ionic liquid.

3. The composition according to claim 2, wherein the fatty acid-based ionic liquid is an equimolar salt of a saturated or unsaturated fatty acid having 3 to 22 carbon atoms and an alkanolamine having 6 to 9 carbon atoms.

4. The composition according to claim 2 further comprising a saturated or unsaturated fatty acid having 10 to 22 carbon atoms.

5. The composition according to claim 3, wherein the saturated or unsaturated fatty acid having 3 to 22 carbon atoms is at least one selected from the group consisting of lactic acid, levulinic acid, decanoic acid, oleic acid, isostearic acid, and myristic acid.

6. The composition according to claim 3, wherein the alkanolamine is at least one selected from the group consisting of triethanolamine, triisopropanolamine, and diisopropanolamine.

7. The composition according to claim 3, wherein the fatty acid-based ionic liquid and/or the salicylic acid-based ionic liquid are at least one selected from the group consisting of triethanolamine lactate, triisopropanolamine lactate, triethanolamine levulinate, diisopropanolamine levulinate, triisopropanolamine decanoate, triethanolamine salicylate, diisopropanolamine oleate, triethanolamine isostearate, diisopropanolamine isostearate, and diisopropanolamine myristate.

8. The composition according to claim 1, wherein the lipophilic plaster base material comprises an elastomeric styrene-isoprene-styrene block copolymer.

9. The composition according to claim 1, wherein the drug is selected from a small molecular medicinal compound, a protein medicine, an antigen peptide, or a nucleic acid derivative.

10. The composition according to claim 1, wherein the organic solvent is contained as shown in the following inequality:

$$\frac{\text{the amount of the solvent to be added}}{(\text{the volume of the solvent to be added})} < \frac{\text{the amount of the powder to be added}}{\text{the tap density of the powder}} \times 1.2.$$
$$(\text{the volume of the powder to be added})$$

11. The composition according to claim 3 further comprising a saturated or unsaturated fatty acid having 10 to 22 carbon atoms.

12. The composition according to claim 1, wherein the only powder in the composition is the anhydrous silicic acid.

* * * * *